(12) United States Patent
Hu et al.

(10) Patent No.: US 9,987,240 B2
(45) Date of Patent: *Jun. 5, 2018

(54) ALL-NATURAL ENTERIC SOFT CAPSULES

(71) Applicant: PATHEON SOFTGELS INC, High Point, NC (US)

(72) Inventors: Yunhua Hu, Cary, NC (US); Martin Piest, Tilburg (NL); Qi Fang, Oak Ridge, NC (US); Henricus M. G. M. van Duijnhoven, den Bosch (NL)

(73) Assignee: Patheon Softgels, Inc., Highpoint, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/718,531

(22) Filed: Sep. 28, 2017

(65) Prior Publication Data

US 2018/0015059 A1    Jan. 18, 2018

Related U.S. Application Data

(60) Continuation of application No. 15/404,368, filed on Jan. 12, 2017, now Pat. No. 9,782,374, which is a
(Continued)

(51) Int. Cl.
*A61K 31/196* (2006.01)
*A61K 31/202* (2006.01)
(Continued)

(52) U.S. Cl.
CPC .......... *A61K 31/196* (2013.01); *A23L 29/284* (2016.08); *A23L 33/12* (2016.08);
(Continued)

(58) Field of Classification Search
None
See application file for complete search history.

(56) References Cited

U.S. PATENT DOCUMENTS

| 4,518,433 A | 5/1985 | Tuason, Jr. |
| 4,719,112 A | 1/1988 | Wittwer |

(Continued)

FOREIGN PATENT DOCUMENTS

| EP | 0888778 A1 | 1/1999 |
| EP | 1072633 A1 | 1/2001 |

(Continued)

OTHER PUBLICATIONS

Fish Oil and Vitamine, Oct. 2, 2012 ([retrieved from on-line website: www.oilofpisces.com/vitamine.html, last visit Apr. 13, 2017]).

*Primary Examiner* — Ernst V Arnold
*Assistant Examiner* — Kyung S Chang
(74) *Attorney, Agent, or Firm* — Brinks Gikson & Lione

(57) ABSTRACT

Described herein are soft capsules and enteric soft capsules comprising cationic Type A gelatin and acid insoluble enteric polymers. In particular, the compositions and methods for manufacturing all-natural enteric soft capsules comprising Type A gelatin and matrix fills are described. In one embodiment, the enteric soft capsules comprise active ingredients such as non-steroidal anti-inflammatory drugs (NSAIDs). In another embodiment, the enteric soft capsule comprises matrix fills of omega-3 fatty acids.

19 Claims, 3 Drawing Sheets

Related U.S. Application Data division of application No. 14/745,485, filed on Jun. 22, 2015, now abandoned.

(60) Provisional application No. 62/015,818, filed on Jun. 23, 2014, provisional application No. 62/015,821, filed on Jun. 23, 2014, provisional application No. 62/065,791, filed on Oct. 20, 2014.

(51) Int. Cl.
    *A61K 35/60* (2006.01)
    *A61K 9/48* (2006.01)
    *A23L 33/12* (2016.01)
    *A23L 29/281* (2016.01)
    *A23P 10/30* (2016.01)

(52) U.S. Cl.
    CPC .............. *A23P 10/30* (2016.08); *A61K 9/485* (2013.01); *A61K 9/4816* (2013.01); *A61K 9/4825* (2013.01); *A61K 9/4833* (2013.01); *A61K 9/4858* (2013.01); *A61K 9/4866* (2013.01); *A61K 9/4875* (2013.01); *A61K 31/202* (2013.01); *A61K 35/60* (2013.01)

(56) References Cited

U.S. PATENT DOCUMENTS

| | | |
|---|---|---|
| 4,816,259 A | 3/1989 | Virgilio |
| 5,146,730 A | 9/1992 | Dietel |
| 5,264,223 A | 11/1993 | Yamamoto |
| 5,330,759 A | 7/1994 | Stetsko |
| 5,431,917 A | 7/1995 | Abe |
| 5,459,983 A | 10/1995 | Dietel |
| 5,478,570 A | 12/1995 | Sunohara |
| 5,484,598 A | 1/1996 | Morton |
| 5,540,912 A | 7/1996 | Roorda |
| 5,629,003 A | 5/1997 | Hungerbach |
| 6,482,516 B1 | 11/2002 | Dietel |
| 8,685,445 B2 | 4/2014 | Hassan |
| 8,962,005 B2 | 2/2015 | Chidambaram |
| 2001/0024678 A1 | 9/2001 | He |
| 2003/0166508 A1 | 9/2003 | Zhang |
| 2003/0175335 A1 | 9/2003 | He |
| 2003/0211146 A1 | 11/2003 | He |
| 2004/0037877 A1 | 2/2004 | Opheim |
| 2004/0105835 A1 | 6/2004 | He |
| 2004/0224020 A1 | 11/2004 | Schoenhard |
| 2004/0265384 A1 | 12/2004 | He |
| 2006/0115527 A1 | 6/2006 | Hassan |
| 2006/0165778 A1 | 7/2006 | Hassan |
| 2007/0148248 A1 | 6/2007 | Chidambaram |
| 2010/0158958 A1 | 6/2010 | Chidambaram |
| 2010/0255085 A1 | 10/2010 | Liu |
| 2010/0278879 A1 | 11/2010 | Manku |
| 2012/0301546 A1 | 11/2012 | Hassan |

FOREIGN PATENT DOCUMENTS

| | | |
|---|---|---|
| EP | 1132081 A2 | 9/2001 |
| EP | 1447082 A1 | 8/2004 |
| EP | 1518552 A1 | 3/2005 |
| JP | 58172313 A2 | 10/1983 |
| JP | 58194810 A2 | 11/1983 |
| JP | 4027352 A2 | 1/1992 |
| JP | 5245366 A2 | 9/1993 |
| WO | 199901115 A1 | 1/1999 |
| WO | 200018835 A1 | 4/2000 |
| WO | 200170385 A2 | 9/2001 |
| WO | 200384516 | 10/2003 |
| WO | 200430658 | 4/2004 |
| WO | 200775475 | 7/2007 |
| WO | 201309363 | 1/2013 |

ALL-NATURAL ENTERIC SOFT CAPSULES

CROSS REFERENCE TO RELATED APPLICATIONS

This application is a continuation of U.S. patent application Ser. No. 15/404,368, filed Jan. 12, 2017, which is a divisional application of U.S. patent application Ser. No. 14/745,485, filed Jun. 22, 2015, which claims priority to U.S. Provisional Patent Application Nos. 62/015,818, and 62/015,821, both filed Jun. 23, 2014, and 62/065,791, filed Oct. 20, 2014, each of which are incorporated by reference herein in its entirety.

TECHNICAL FIELD

Described herein are soft capsules and enteric soft capsules comprising cationic Type A gelatin and acid insoluble enteric polymers. In particular, the compositions and methods for manufacturing all-natural enteric soft capsules comprising Type A gelatin and matrix fills are described. In some embodiments, the enteric soft capsules comprise active ingredients such as non-steroidal anti-inflammatory drugs (NSAIDs) or omega-3 fatty acids.

BACKGROUND

The use and manufacture of oral enteric dosage forms are known in the art. Such dosage forms have been explained and reviewed in reference works, e.g., in *Remington's Pharmaceutical Sciences*, 18$^{th}$ edition, Mack Publishing Co., Easton, Pa. (1990). Enteric dosage forms are desirable, either to protect the content of the dosage form from the gastric conditions or to protect the gastric tissue from an irritant material contained in the enteric dosage form. The protection of gastric and esophageal tissues using enteric dosage forms is very important for the sustained use of non-steroidal anti-inflammatory drugs in conditions such as chronic pain, osteoarthritis, and rheumatoid arthritis.

A further use for enteric dosages is for the prevention of a lasting, unacceptable mouth odor resulting from ingestion of substances like garlic or fish oil. Furthermore, in some cases all-natural fish oil capsules containing omega-3 fatty acids are desirable to consumers.

Enteric dosage forms are also used to provide slow, controlled, or delayed release of a substance.

To fulfill the compendium definition requirement for enteric or gastro-resistant preparations, these preparations have to pass specific compendia tests. The enteric or gastro-resistant property is obtained only if the enteric dosage form does not dissolve or disintegrate in gastric acidity for a specified amount of time (usually two hours in 0.1 N hydrochloric acid, pH ca. 1.2 at 37° C.). Further, the enteric dosage forms must release their contents in simulated intestinal environments (e.g., in buffers of pH values at about 6.8) within certain time periods. Detailed evaluation techniques are described in national and international pharmacopoeia.

The majority, if not all, of the enteric dosage forms currently in use are produced by a film-coating process, where a thin film layer of acid-insoluble (enteric) polymer is accumulated on the surface of a pre-manufactured dosage form. Dosage forms coated in this manner have been mainly tablets and, to a lesser extent, hard or soft capsules. The enteric coating method involves spraying of an aqueous or organic solution or a suspension of enteric polymers onto tumbling or moving tablets or capsules, accompanied by drying using hot air.

Enteric dosage forms made by coating suffer from various process-related problems and defects that affect their performance or appearance. For example, "orange peel" surface formation, also known as surface roughness, mottling, or lack of surface homogeneity may result. In addition, coat integrity failure may occur, such as in cases of cracking or flaking of the coating. All coatings present inherent problems, including possible uneven distribution of the coating ingredients, which can easily happen under the multivariate coating process. These failures of enteric coatings reduce the effectiveness of said coating in preventing painful and often harmful gastric and esophageal disturbances.

The foregoing problems of enteric coatings are shared by all enteric dosage forms such as tablets and capsules. However, the problems faced during coating of capsules are even more critical, due to the delicate and heat sensitive nature of the soft elastic capsule shell. Both hard and soft capsules can easily undergo agglomeration and distortion due to the heat-sensitive shell composition. Moreover, the smoothness and elasticity of the capsule surface make it difficult to form an intact adhering enteric coat without careful sub-coating steps to improve the surface for coating. A further disadvantage of enteric coating for soft capsules is the loss of the normally shiny and clear appearance of capsule gelatin shells. The elegant, clear gelatin shell has been a significant reason for soft capsule popularity and acceptance. In addition to the undesirable surface texture modifications usually caused by coating, most accepted aqueous enteric polymer preparations result in opaque capsules.

Medical professionals are increasingly recognizing the positive cardiovascular health benefits of fish oil based products. The principle oral dosage of fish oil is through soft gelatin capsules. However, a major limitation for consumers and patient compliance for the continued taking of these fish oil products is the presence of disruptive and unpleasant fishy odors associated with these traditional soft gelatin fish oil capsules. In particular, taking fish oil can result in negative side effects, including but not limited to, gastric disturbances such as fishy eructation (belching, e.g., "fishy burps"), gastrointestinal discomfort, bloating, nausea, diarrhea, unpleasant fishy odor, or unpleasant fishy aftertaste.

To minimize these negative side effects, consumers often will freeze their fish oil capsules before ingestion, which is thought to potentially prevent break down of the capsule in the esophagus and stomach. Several commercial products offer enterically coated fish oil soft gelatin capsules to help circumvent capsule break down in the stomach. Other products include flavors or odor masking agents such as citrus or vanilla. However, these agents do not solve the negative side effects. In addition, there are significant problems associated with traditional enteric coated capsules.

In addition, consumers have expressed a desire for nutraceuticals or dietary supplements made of all-natural ingredients. Thus, compositions promoting "All-Natural Ingredients" are appealing to nutrition-conscious consumers compared to products containing artificial ingredients.

Accordingly, it is desirable to develop an oral delivery system that provides enteric properties and that utilize all-natural ingredients, especially for use with fish oil or non-steroidal anti-inflammatory drugs.

Therefore, the enteric oral soft capsules described herein, have robust acid-resistant capsule shells, and are not enterically coated. Moreover, the soft capsules described herein, are easy to ingest.

SUMMARY

Described herein are compositions and methods for manufacturing for all-natural oral enteric soft capsules.

One embodiment described herein is an all-natural enteric soft capsule shell composition comprising: (a) a gelatin composition; (b) an anionic polysaccharide; (c) a plasticizer; and (d) a solvent. In one aspect described herein: (a) the gelatin composition comprises Type A gelatin having a Bloom strength of 175 grams; (b) the anionic polysaccharide comprises pectin; (c) the plasticizer comprises glycerol; and (d) the solvent comprises water. In one aspect described herein: (a) the gelatin composition comprises pig skin Type A gelatin comprising 33.2% of the total composition or acid bone Type A gelatin comprising 36% of the total composition; (b) the anionic polysaccharide comprises pectin comprising about 3.3% of the total composition; (c) the plasticizer comprises glycerol comprising about 16% of the total composition; and (d) the solvent comprises water comprising about 47% or about 44% of the total composition. In one aspect described herein: (a) the gelatin composition comprises about 33.2% pig skin Type A gelatin; (b) the anionic polysaccharide comprises about 3.3% pectin; (c) the plasticizer comprises about 16% glycerol; and (d) the solvent comprises about 47% water.

Another embodiment described herein is an enteric soft capsule comprising a shell comprising the compositions as described herein. In one aspect described herein, the enteric soft capsule comprises a matrix fill that is liquid, semi-solid, or solid. In one aspect described herein, the enteric soft capsule shell does not dissolve in simulated gastric fluid (pH 1.2) for at least 2 hours, and begins dissolution in simulated intestinal fluid (pH 6.8) within about 10 minutes. In one aspect described herein, the enteric soft capsule shell is clear or transparent. In one aspect described herein, the enteric soft capsule shell is transparent and colored. Another embodiment described herein is a method for preparing an all-natural enteric soft capsule shell comprising: (a) combining dry shell components comprising a gelatin composition and an anionic polymer together to form a dry mixture; (b) adding plasticizer and solvent to the dry mixture with agitation to form a wet mixture; (c) heating the wet mixture with agitation and applying vacuum deaeration to form a gel mass; (d) heating the gel mass for an additional period; (e) forming an enteric soft capsule using rotary die technology; and (f) drying the enteric soft capsules. In one aspect described herein, the wet mixture is heated to about 30° C. to about 90° C. prior to vacuum deaeration. In one aspect described herein, the wet mixture is heated to about 75° C. to about 90° C. prior to vacuum deaeration. In one aspect described herein, the temperature is maintained for a period of about 15 minutes to about 60 minutes. In one aspect described herein, the vacuum deaeration is applied for between about 1 hours to about 6 hours to form a gel mass. In one aspect described herein, the gel mass is heated to about 75° C. to about 90° C. for between about 0.5 hours to about 72 hours.

Another embodiment described herein is an all-natural enteric soft capsule formed according to the method described herein, wherein the final moisture content of the all-natural enteric soft capsule shell after the drying step is from about 5% to about 16%. In one aspect described herein the capsule further comprises an active ingredient in the matrix fill. In one aspect described herein, the all-natural enteric soft capsule shell is stable at pH 1.2 for at least 2 hours. In one aspect described herein, the all-natural enteric soft capsule shell dissolves at pH 6.8 within 30 minutes. In one aspect described herein, the all-natural enteric soft capsule comprises a matrix fill that is liquid, semi-solid, or solid. In one aspect described herein, the all-natural enteric soft capsule shell is clear or transparent. In one aspect described herein, the all-natural enteric soft capsule shell is transparent and colored. In one aspect described herein, the thickness of the all-natural enteric soft capsule shell is from about 0.010 inches to about 0.050 inches.

Another embodiment described herein is a pharmaceutical composition comprising an all-natural enteric soft capsule as described herein.

Another embodiment described herein is a method for treating, ameliorating the symptoms of, or delaying the onset of a medical condition by providing a subject in need thereof with the pharmaceutical composition described herein, further comprising an active pharmaceutical ingredient or a nutraceutical.

Another embodiment described herein is a soft capsule pharmaceutical composition comprising a matrix fill comprising: (a) at least one solubility enhancing agent; (b) at least one plasticizer; (c) water; and (d) at least one active pharmaceutical ingredient. In one aspect described herein, the one or more solubility enhancing agents comprises about 10% to about 85% of the matrix fill mass. In one aspect described herein, the one or more solubilizing plasticizers comprises about 2.5% to about 10% of the matrix fill mass. In one aspect described herein, water comprises about 2.5% to about 20% of the matrix fill mass. In one aspect described herein, the one or more active pharmaceutical ingredients comprises about 5% to about 80% of the matrix fill mass. In one aspect described herein: (a) the one or more solubility enhancing agents comprises polyethylene glycol having a molecular weight of about 200 to about 800; (b) the one or more solubilizing plasticizers comprises glycerol or propylene glycol; (c) the one or more active pharmaceutical ingredients comprises a non-steroidal anti-inflammatory drug. In one aspect described herein: (a) the one or more solubility enhancing agent comprises polyethylene glycol have a molecular weight of about 600 comprising about 80% of the matrix fill mass; (b) the one or more solubilizing plasticizer comprises glycerol comprising about 5% of the matrix fill mass or propylene glycol comprising about 5% of the matrix fill mass; (c) water comprises about 5% of the matrix fill mass; and (d) the one or more active pharmaceutical ingredient comprises diclofenac potassium comprising about 11% of the matrix fill mass.

Another embodiment described herein is a method for preparing matrix fills as described herein comprising sequentially combining the matrix fill components comprising polyethylene glycol having a molecular weight of about 600, propylene glycol, water, and diclofenac potassium and heating the wet mixture under agitation until a clear or transparent solution is observed.

Another embodiment described herein is a soft capsule pharmaceutical composition comprising a matrix fill comprising: (a) at least one wetting agent; (b) at least one lipophilic liquid; (c) at least one semi-solid lipophilic substance; (d) at least one hydrophilic polysaccharide; (e) at least one hydrophilic polymer; and (f) at least one active pharmaceutical ingredient. In one aspect described herein, the one or more wetting agents comprises about 1% to about 3% of the matrix fill mass. In one aspect described herein, the one or more lipophilic liquids comprises about 20% to about 70% of the matrix fill mass. In one aspect described herein, the one or more semi-solid liquid substances comprises about 2% to about 7% of the matrix fill mass. In one aspect described herein, the one or more hydrophilic polysaccharides comprises about 2% to about 10% of the matrix fill mass. In one aspect described herein, the one or more hydrophilic polymers comprises about 2% to about 10% of the matrix fill mass. In one aspect described herein, the active pharmaceutical ingredient comprises about 60% of the matrix fill mass.

Another embodiment described herein, (a) the one or more wetting agents comprises lecithin; (b) the one or more lipophilic liquids comprises vegetable oil and soybean oil; (c) the one or more semi-solid lipophilic substances comprises bee's wax; (d) the one or more hydrophilic polysaccharides comprises chitosan; (e) the one or more hydrophilic polymers comprises Carbopol® 971; and (f) the one or more active pharmaceutical ingredients comprises a non-steroidal anti-inflammatory drug. In one aspect described herein, (a) the wetting agent comprises lecithin comprising about 1.5% of the matrix fill mass; (b) the lipophilic liquid comprises vegetable oil comprising about 12.5% of the matrix fill mass and soybean oil comprising about 53% of the matrix fill mass; (c) the semi-solid lipophilic substance comprises bee's wax comprising about 3% of the matrix fill mass; (d) the hydrophilic polysaccharide comprises chitosan comprising about 5% of the matrix fill mass; (e) the hydrophilic polymer comprises Carbopol® 971 comprising about 5% of the matrix fill mass; and (f) the active pharmaceutical ingredient comprises diclofenac potassium comprising about 20% of the matrix fill mass.

Another embodiment described herein is a method for preparing matrix fills as described herein comprising: (a) combining the specified amounts of wetting agent, lipophilic liquids, semi-solid lipophilic substance to form a first mixture; (b) heating said first mixture to 65° C. under agitation; (c) adding the specified amounts of hydrophilic polymer, hydrophilic polysaccharide, and active pharmaceutical ingredient to the said heated first mixture to form a second mixture; and (d) mixing and de-airing said second mixture to form a matrix fill. In one aspect described herein, the non-steroidal anti-inflammatory drug comprises diclofenac in its salt or free acid form comprising diclofenac potassium, diclofenac sodium, diclofenac hydrochloride, or diclofenac free acid. In one aspect described herein, diclofenac comprises a weight of about 25 mg to about 150 mg. In one aspect described herein, wherein the matrix fill mass is about 80 mg to about 500 mg.

Another embodiment described herein is an oral pharmaceutical composition comprising an enteric soft capsule shell comprising: (a) a gelatin composition comprising a Type A gelatin; (b) at least one acid-insoluble polymer or anionic polysaccharide comprising a methacrylic acid copolymer (e.g., EUDRAGIT® L 100) or pectin; (c) at least one plasticizer comprising glycerol; (d) optionally at least one alkali neutralizing agent comprising ammonia; and (e) water; wherein, the oral pharmaceutical composition further comprises a matrix fill comprising: (a) at least one solubility enhancing agent comprising polyethylene glycol 600; (b) at least one plasticizer comprising glycerol; (c) water; and (d) at least one active pharmaceutical ingredient comprising a non-steroidal anti-inflammatory drug; or (e) one or more wetting agents comprising lecithin; (f) one or more lipophilic liquids comprising vegetable oil and soybean oil; (g) one or more semi-solid lipophilic substances comprising bee's wax; (h) one or more hydrophilic polysaccharides comprising chitosan; (i) one or more hydrophilic polymers comprising Carbopol® 971; and (j) one or more active pharmaceutical ingredients comprising a non-steroidal anti-inflammatory drug.

Another embodiment described herein is an oral pharmaceutical composition comprising an enteric soft capsule shell comprising: (a) pig skin Type A gelatin comprising about 33.2% of the shell mass or acid bone Type A gelatin comprising about 36% of the shell mass; (b) pectin comprising about 3.3% of the total gel mass or EUDRAGIT® L 100 comprising about 11% of the shell mass; (c) a plasticizer comprising glycerol comprising about 16% or about 18% of the shell mass; (d) an optional alkali neutralizing agent comprising about 1.7% of the shell mass; and (e) a solvent comprising about 47% or about 44% of the shell mass; and wherein, the oral pharmaceutical composition further comprises a matrix fill comprising: (a) polyethylene glycol 600 comprising about 80% of the matrix fill mass; (b) propylene glycol comprising about 5% of the matrix fill mass; (c) water comprising about 5% of the matrix fill mass; and (d) diclofenac potassium comprising about 11% of the matrix fill mass; or (e) lecithin comprising about 1.5% of the matrix fill mass; (f) vegetable oil comprising about 12.5% of the matrix fill mass and soybean oil comprising about 53% of the matrix fill mass; (g) bee's wax comprising about 3% of the matrix fill mass; (h) chitosan comprising about 5% of the matrix fill mass; (i) Carbopol® 971 comprising about 5% of the matrix fill mass; and (j) diclofenac potassium comprising about 20% of the matrix fill mass.

Another embodiment described herein is an all-natural oral enteric pharmaceutical composition comprising a soft enteric capsule shell and a matrix, the capsule shell comprising: (a) a gelatin composition; (b) at least one or more anionic polymer; (c) at least one or more plasticizer; and (d) water; and the matrix fill comprising: (e) one or more fatty acids, one or more fat-soluble vitamins, or a combination thereof. In one aspect described herein, the fatty acid comprises omega-3 fatty acids, polyunsaturated omega-3 fatty acids, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA), clupanodonic acid), docosahexaenoic acid (DHA, cervonic acid), tetracosapentaenoic acid, tetracosahexaenoic acid (nisinic acid), arachidonic acid and free acids, etheyl esters, or other esters or salts and combinations thereof. In one aspect described herein, the all-natural enteric soft capsule size is defined as being from about 2 oval to about 8 oval or about 2 round to about 8 round. In one aspect described herein, the composition is useful for treating, retarding the progression of, delaying the onset of, prophylaxis of, amelioration of, or reducing the symptoms a medical condition.

Another embodiment described herein is a method for treating, retarding the progression of, delaying the onset of, prophylaxis of, amelioration of, or reducing the symptoms of a medical condition by administering to a subject in need thereof the pharmaceutical composition described herein.

Another embodiment described herein is a method for treating, retarding the progression of, delaying the onset of, prophylaxis of, amelioration of, or reducing the symptoms of mild, moderate, or severe pain stemming from arthritis, tendonitis, bursitis, dysmenorrhea, endometriosis, chronic neuropathies, shingles, sports injuries, cancer, or malignancies; inflammation; mild, moderate, or severe fever; migraines; osteoarthritis; rheumatoid arthritis; ankylosing spondylitis; spondylarthritis; gout; pain associated with kidney stones; or a combination thereof, the method comprising administering to a subject in need thereof the oral pharmaceutical composition, without substantially inducing one or more of esophageal irritation, esophageal erosion, gastric irritation, gastric reflux, or peptic ulcers.

Another embodiment described herein is a method for treating, retarding the progression of, delaying the onset of, prophylaxis of, amelioration of, or reducing the symptoms of a cardiovascular-related disease including, but not limited to, hyperlipidemia or hypertriglyceridemia, the method comprising administering to a subject in need thereof the oral pharmaceutical composition as described herein, without substantially inducing one or more of one or more of eructation, abdominal discomfort, nausea, diarrhea, or unpleasant fishy odor.

Another embodiment described herein is a kit for dispensing the oral pharmaceutical composition as described herein, comprising: (a) at least one enteric soft capsule comprising a matrix fill that further comprises at least about 25 mg to about 500 mg of an active pharmaceutical ingredient; (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; (c) optionally, an insert comprising instructions or prescribing information for the active pharmaceutical ingredient.

DETAILED DESCRIPTION

Figure 1:
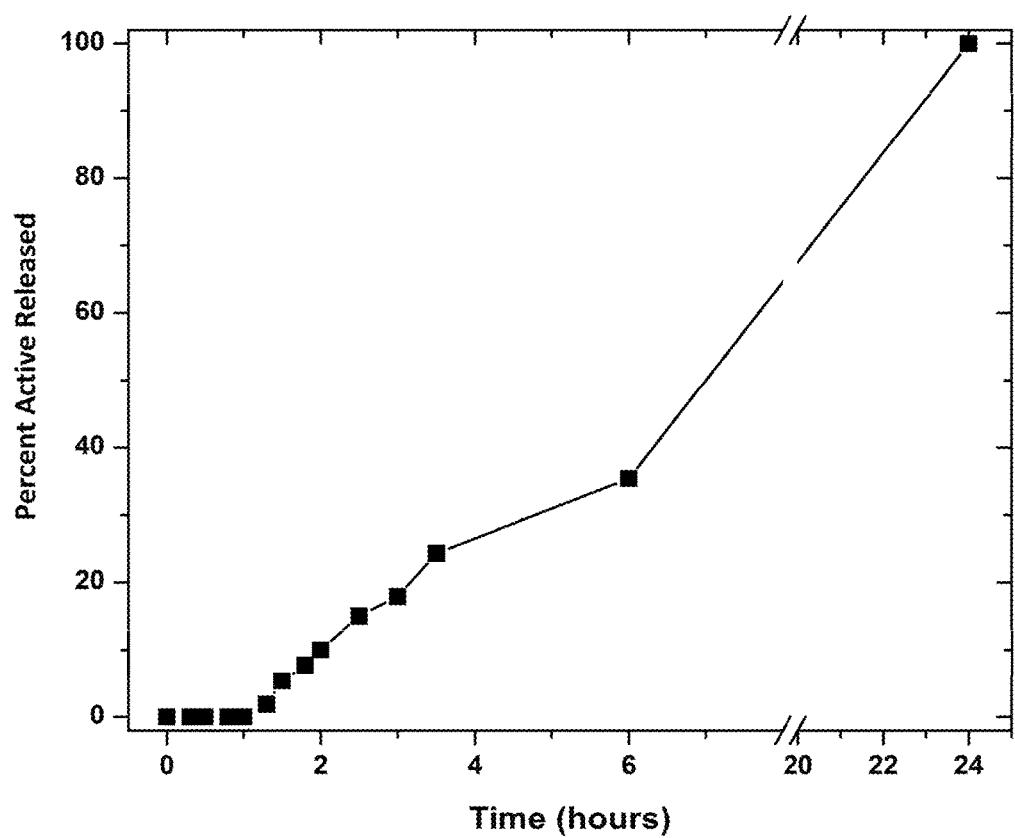
FIG. 1. Delayed release of enteric soft capsules comprising the composition of Table 16.

Described herein are compositions and methods for manufacturing soft capsules containing gelatin that are in some aspects made of all-natural ingredients.

As used herein, the term "all-natural" refers to the enteric soft capsule shell and means that the enteric soft capsule shell does not comprise any synthetic or artificial components.

As used herein, the phrase "pharmaceutical composition" encompasses "nutritional compositions" or "nutritional supplements."

As used herein, the terms "gastric-resistant" and "enteric" are used interchangeably and refer to the property of a substance resistant dissolution in biological, artificial, or simulated gastric fluid (pH ca. 1.2), and that dissolves in biological, artificial, or simulated intestinal fluid (pH ca. 6.8). One embodiment described herein is gastric-resistant or enteric soft capsules.

As used herein, the term "fatty acid" refers to any carboxylic acid having a long aliphatic chain that can be either saturated or unsaturated. The term fatty acid further encompasses any fish oil described herein and any saturated, polyunsaturated, monounsaturated, or any omega-3, -6, -7, or -9 fatty acid.

As used herein, the term "bioavailability" refers to the proportion of an active pharmaceutical ingredient that enters the systemic circulation when introduced into the body and is able to have a physiological effect.

As used herein, the term "enhanced bioavailability" refers to the increased proportion of an active pharmaceutical ingredient that enters the systemic circulation when introduced into the body as compared to a reference's bioavailability.

As used herein, the term "absolute bioavailability" refers to the fraction of a drug or active pharmaceutical ingredient absorbed through non-intravenous administration (e.g., oral administration) as compared to intravenous administration of the same drug or active pharmaceutical ingredient.

As used herein, the term "polyunsaturated fatty acid" ("PUFA") refers to a long chain fatty acid that contains more than one double bond in the backbone of the chain. The term encompasses esters, re-esterified triglycerides, or salts thereof.

As used herein, the term "monounsaturated fatty acid" refers to a long chain fatty acid that contains only one double bond in the backbone of the chain. The term encompasses esters, re-esterified triglycerides, or salts thereof.

As used herein, the terms "active ingredient," "active pharmaceutical ingredient," or "active pharmaceutical agent" refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable free acids, free bases, salts, or esters.

As used herein, the terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

As used herein, the phrase "enteric soft capsule composition," "enteric soft capsule," "enteric soft capsule gel mass," "gel mass," or "enteric soft capsule shell" are used interchangeably and have the same meaning. Typically, as used herein, "enteric soft capsule composition" or "gel mass" refer to enteric soft capsule compositions prior to forming the enteric soft capsule and "enteric soft capsule shell" refers to the enteric capsule shell after having been formed into an enteric soft capsule, for example, by using rotary die encapsulation. When the phrases "enteric soft capsule composition," "enteric soft capsule," "enteric soft capsule gel mass," "gel mass," or "enteric soft capsule shell" are used herein without the preceding phrase "all-natural," the shell may contain synthetic or artificial components.

As used herein, the terms "matrix," "matrix composition," "matrix fill," "fill composition," or "fill" all refer to a composition that is encapsulated by a capsule shell and may optionally contain an active pharmaceutical ingredient.

As used herein, the term "pharmaceutical composition" refers a composition comprising at least on active ingredient, nutraceutical, nutritional, or vitamin. In some embodiments described herein, a pharmaceutical composition comprises a soft capsule shell having been formed into a capsule, for example, using rotary die encapsulation comprising one or more polyunsaturated fatty acids, optionally with one or more vitamins, antioxidants, or other active ingredients.

The term "formulation" or "composition" as used herein refers to the active pharmaceutical ingredient, nutraceutical, nutritional, vitamin, or drug in combination with pharmaceutically acceptable excipients. This includes orally administrable formulations as well as formulations administrable by other means.

The term "controlled release" as used herein refers to a composition that does not immediately release an active ingredient. "Controlled release" as used herein encompasses the terms "modified release," "sustained release," "extended release," and "delayed release."

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours; about 24 hours; or even longer.

The term "modified release" as used herein refers to a composition that releases an active ingredient at a slower rate than does an immediate release formulation under physiological conditions or in an in vitro test.

The term "sustained" release as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically over a period of at least 18 hours under physiological conditions or in an in vitro assay.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "room temperature" as used herein refers to common ambient temperatures ranging from about 20° C. to about 27° C.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any values, including both integers and fractional components that are within a variation of up to ±10% of the value modified by the term "about." For example, the phrase "about 50%" is equivalent to any vale ≈50±10%, e.g., 44.6%, 45%, 46%, 47%, 48%, 49%, 49.5%, 50%, 50.3%, 51%, 52%, 53%, 54%, 55%, inter alia.

As used herein, "a" or "an" means one or more unless otherwise specified.

Terms such as "include," "including," "contain," "containing," "has," or "having," and the like, mean, "comprising."

The term "or" can be conjunctive or disjunctive.

One embodiment described herein is an all-natural enteric soft capsule composition comprising a gelatin composition ionically bonded with anionic enteric polymers. The enteric soft capsule shell can comprise one or more types of gelatin, one or more anionic enteric polymers, one or more plasticizers, one or more solvents, and optionally colorings, gelling agents, flavorings, or other conventionally accepted pharmaceutical excipients or additives.

The all-natural enteric soft capsules described herein can be used for oral delivery of active pharmaceutical ingredients, nutraceuticals, or nutritionals that are irritating to the stomach, that are sensitive to the acidity of the stomach, or that have unpleasant tastes or odors. The enteric soft capsules described herein do not dissolve in the gastric environment (pH ca. 1.2), but readily dissolve in the intestinal environment (pH ca. 6.8).

Enteric soft capsules are described generally in International Patent Application Publication Nos. WO 2004/030658 and WO 2007/075475 and U.S. Patent Application Publication Nos. US 2006/0165778 and US 2010/0158958, each of which is incorporated by reference herein for such teachings. The enteric soft capsule shell can comprise one or more film forming polymers, one or more enteric acid insoluble polymers, one or more plasticizers, one or more alkali neutralizing agents, one or more solvents, optionally one or more colorants, and optionally one or more flavorings and/or other conventionally accepted pharmaceutical excipients or additives.

Film-former polymers that are useful for creating enteric soft capsules are gelatin or hydroxypropylmethylcellulose (HPMC). In one aspect of the enteric soft capsule shell described herein, the film-forming polymer is gelatin. Examples of gelatin compositions that are useful for creating enteric soft capsules described herein comprise acid bone gelatin, lime bone gelatin, pig skin gelatin, chicken skin gelatin, fish gelatin, acid hide gelatin, gelatin hydrolysate, or combinations thereof. The strength of said gelatin compositions are often defined by their Bloom strength or grade in the range of about 30 Bloom to about 400 Bloom.

Examples of enteric, anionic polysaccharides, as described herein, comprise polygalacturonic acid, carboxymethyl pullulan, carboxymethyl cellulose, hyaluronic acid, cellulose phthalate, cellulose succinate, alginate, sodium alginate, and pectin, acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs. Without being bound by any theory, it is believed that the acid-insoluble properties of the gel mass and resulting capsule shell is derived from the intermolecular ionic interactions between the positively charged Type-A gelatin and the negatively charged anionic polysaccharide; thus, such formulations obviate the need for any crosslinking or gelling agents. Acid-insoluble specifications of enteric capsules are detailed in the United States Pharmacopoeia, which is incorporated by reference herein for such teachings.

Useful plasticizers as described herein comprise glycerol, sorbitol, Sorbitol Special® (SPI Pharma), non-crystallizing sorbitol, Polysorb® sorbitol 85/70/00 (Roquette), maltitol, corn syrup, polyethylene glycol, 1,2-propylene glycol, acetyltriethyl citrate, dibutyl phthalate, dibutyl sebacate, triacetine, polydextrose, dextrose, maltodextrin, citric acid, citric acid esters, such as triethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one particular embodiment described herein, the plasticizer comprises at least one of glycerol, sorbitol, or mixtures or combinations thereof. In one embodiment, optional gelling agents can be added to the enteric soft capsules. The addition of gelling agents is optional and depends on the gelatin type (e.g., Type B gelatin), which may function to increase the overall strength of the capsule shell. Without being bound to any theory, it is believed that the cationic gelling agent promotes an ionic interaction between the gelatin composition and the anionic enteric polymer. Suitable gelling agents as described herein comprise mono or divalent cations, such as calcium, sodium, potassium, magnesium, or their salt forms comprising calcium sulfate, sodium chloride, potassium sulfate, sodium carbonate, lithium chloride, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

In one embodiment described herein, the all-natural enteric soft capsule shell has the composition of Table 1, including all possible iterations of the specified ranges that provide 100% for the total weight percentage, including or excluding the optional colorings, flavorings, or excipients.

TABLE 1

All-natural Enteric Soft Capsule Shell Composition

| Component | Exemplary Components | Composition Range (%) |
|---|---|---|
| Gelatin composition | Type A Gelatin or Type A Gelatin + Type B Gelatin or Type A Gelatin + Gelatin Hydrolysate | 20-40 (Type A: 25-37/Type B: 32-37/Gel. Hydro: 28-36) |
| Enteric anionic polymer | Anionic polysaccharide (e.g., pectin) | 2-7 |
| Plasticizer | Glycerol, Sorbitol, Triethyl citrate | 8-30 |
| Gelling agent | Calcium, Magnesium, Potassium | 0.001-0.05 |
| Solvent | Water | 40-70 |
| Opacifier (optional) | Titanium dioxide | 0.5-5 |
| Coloring (optional) | Various | 0.005-1 |
| Flavoring (optional) | Various | 0.005-2 |
| Excipients (optional) | Various | 1-5 |

In another embodiment described herein, the weight percentage of the total gelatin composition in the all-natural enteric soft capsule composition is about 25% to about 37% including all integers within the specified range. In another embodiment, the weight percentage of the gelatin composition in the gel mass is about 32% to about 37% including all integers within the specified range. In another embodiment, the weight percentage of the gelatin composition in the gel mass is about 28% to about 36%. In one aspect, the weight percentage of the gelatin composition in the gel mass is about 33%.

In another embodiment described herein, the weight percentage ratio range of Type A gelatin to Type B gelatin in the all-natural enteric soft capsule composition is about 2:1 to about 11:1, including all ratios within the specified range. In one aspect, the weight percentage ratio range of Type A gelatin to Type B gelatin in the gel mass is about 6:1. In another aspect, the ratio of Type A gelatin to Type B gelatin in the gel mass is about 3:1.

In another embodiment described herein, the weight percentage ratio of Type A gelatin to gelatin hydrolysate in the all-natural enteric soft capsule composition is about 10:1 to about 35:1, including all ratios within the specified range. In one aspect, the weight percentage ratio of Type A gelatin to gelatin hydrolysate in the gel mass is about 12:1, including all integers within the specified range. In another aspect, the ratio of Type A gelatin to gelatin hydrolysate in the gel mass is about 27:1.

In one embodiment described herein, all-natural enteric soft capsule compositions comprising Type A gelatin in the all-natural enteric soft capsule gel mass are preferable to all-natural enteric soft capsule compositions comprising Type A gelatin and Type B gelatin in the all-natural enteric soft capsule gel mass. In another embodiment described herein, all-natural enteric soft capsule compositions comprising Type A gelatin are preferable to all-natural enteric soft capsule compositions comprising Type A gelatin and gelatin hydrolysate in the all-natural enteric soft capsule gel mass. In one aspect described herein, all-natural enteric soft capsule compositions described herein are comprised of Type A gelatin in the all-natural enteric soft capsule gel mass.

In another embodiment described herein, the weight percentage of Type A gelatin in the all-natural enteric soft capsule composition is about 22% to about 38%, including all integers within the specified range. In another embodiment, the weight percentage of Type A gelatin in the gel mass is about 28% to about 36%, including all integers within the specified range. In one aspect, the weight percentage of Type A gelatin in the gel mass is about 28%. In another aspect, the weight percentage of Type A gelatin in the gel mass is about 31%. In another aspect, the weight percentage of Type A gelatin in the gel mass is about 33%.

In another embodiment described herein, the weight percentage of Type B gelatin in the all-natural enteric soft capsule composition is about 0.01% to about 10%, including all integers within the specified range. In another embodiment, the weight percentage of Type B gelatin in the gel mass is about 0.01% to about 7%, including all integers within the specified range. In one aspect, the weight percentage of Type B gelatin in the gel mass is about 3%. In another aspect, the weight percentage of Type B gelatin in the gel mass is about 7%. In another aspect, the weight percentage of Type B gelatin in the gel mass is about 9%.

In another embodiment described herein, the weight percentage range of anionic polymer in the all-natural enteric soft capsule composition is about 2% to about 7%, including all integers within the specified range. In one aspect, the weight percentage of anionic polymer in the gel mass is about 2.8%. In another aspect, the weight percentage of anionic polymer in the gel mass is about 3.1%. In another aspect, the weight percentage of anionic polymer in the gel mass is about 3.3%. In another aspect, the weight percentage of anionic polymer in the gel mass is about 5%. In another aspect, the weight percentage of anionic polymer in the gel mass is about 6.8%.

In one embodiment described herein, the weight percentage range of total ionically bonded polymer content (i.e., total gelatin content and anionic polymer) of the enteric soft capsule composition described herein is about 28% to about 41%, including all integers within the specified range. In one aspect, the total ionically bonded polymer weight percentage in the gel mass is about 31%. In another aspect, the total ionically bonded polymer weight percentage in the gel mass is about 35%. In another aspect, the total ionically bonded polymer weight percentage in the gel mass is about 40%.

In another embodiment described herein, the weight percentage range of total plasticizer in the all-natural enteric soft capsule composition is about 8% to about 20%, including all integers within the specified range. In one aspect, the weight percentage of plasticizer in the gel mass is about 12%. In another aspect, the weight percentage of plasticizer in the gel mass is about 14%. In another aspect, the weight percentage of plasticizer in the gel mass is about 17%.

In another embodiment described herein, the weight percentage range of gelling agent of the enteric soft capsule composition described herein is about 0.001% to about 0.05%, including all integers within the specified range. In one aspect, the weight percentage of the gelling agent in the gel mass is about 0.003%. In another aspect, the weight percentage of the gelling agent in the gel mass is about 0.006%.

In one embodiment described herein, the weight percentage ratio range of total gelatin to anionic polymer of the enteric soft capsule composition described herein is about 4:1 to about 19:1, including all ratios within the specified range. In one aspect, the weight percentage ratio of total gelatin to anionic polymer in the gel mass is about 4:1. In one aspect, the weight percentage ratio of total gelatin to anionic polymer in the gel mass is about 6:1. In one aspect, the weight percentage ratio of total gelatin to anionic polymer in the gel mass is about 10:1. In one aspect, the weight percentage ratio of total gelatin to anionic polymer in the gel mass is about 12:1. In one aspect, the weight percentage ratio of total gelatin to anionic polymer in the gel mass is about 15:1. In one aspect, the weight percentage ratio of total gelatin to anionic polymer in the gel mass is about 19:1.

In one embodiment described herein, the weight percentage ratio range of total gelatin to plasticizer of the enteric soft capsule composition described herein is about 1.5:1 to about 4.5:1, including all ratios within the specified range. In one aspect, the weight percentage ratio of total gelatin to plasticizer in the gel mass is about 2:1. In one aspect, the weight percentage ratio of total gelatin to plasticizer in the gel mass is about 3:1. In one aspect, the weight percentage ratio of total gelatin to plasticizer in the gel mass is about 4:1.

In one embodiment described herein, the weight percentage ratio range of plasticizer to anionic polymer of the enteric soft capsule composition described herein is about 2:1 to about 8:1, including all ratios within the specified range. In one aspect, the weight percentage ratio of plasticizer to anionic polymer in the gel mass is about 3:1. In one aspect, the weight percentage ratio of plasticizer to anionic polymer in the gel mass is about 4:1. In one aspect, the weight percentage ratio of plasticizer to anionic polymer in the gel mass is about 6:1. In one aspect, the weight percentage ratio of plasticizer to anionic polymer in the gel mass is about 8:1.

In one embodiment described herein, the solvent comprises about 40% to about 70% of the wet enteric soft capsule composition, including all integers within the specified range. In one aspect, the solvent is water. The quantity of water in the composition varies depending on the quantities of the other ingredients. For example, the quantity of opacifier, coloring, flavoring, or other excipients can change the percentage of water present in the composition. In one embodiment, the weight percentage of water is as much as suffices to bring the total weight percentage to 100% (i.e., quantum sufficiat; q.s.). In another embodiment, the water comprises about 60%, about 50%, or about 40%, of the wet enteric soft capsule composition. In another embodiment, water comprises about 42% of the wet enteric soft capsule composition. In another embodiment, water comprises about 55% of the wet enteric soft capsule composition.

In one embodiment described herein, the final moisture (water) content of the enteric soft capsule shell formed from the compositions described herein is adequately adjusted prior to vacuum deaeration. In another embodiment, an additional 1% to about 10% by weight of water, including all integers within the specified range, is added to the gel mass adjusted prior to vacuum deaeration. In another embodiment, an additional 1% to about 5% by weight of water, including all integers within the specified range, is added to the gel mass adjusted prior to vacuum deaeration. In one aspect, an additional 3% by weight of water is added to the gel mass adjusted prior to vacuum deaeration.

In one aspect, the final moisture content of the enteric soft capsule shell after vacuum deaeration and drying is from about 5% to about 25% including all integers within the specified range. In another aspect, the final moisture content of the enteric soft capsule shell after vacuum deaeration and drying is from about 5% to about 16% including all integers within the specified range. In another aspect, the final moisture content of the enteric soft capsule shell after vacuum deaeration and drying is from about 8% to about 12% including all integers within the specified range. In another aspect, the final moisture content of the enteric soft capsule shell after vacuum deaeration and drying is about 5%. In another aspect, the final moisture content of the enteric soft capsule shell after vacuum deaeration and drying is about 8%. In another aspect, the final moisture content of the enteric soft capsule shell after vacuum deaeration and drying is about 12%. In another aspect, the final moisture content of the enteric soft capsule shell after vacuum deaeration and drying is about 13%. In another aspect, the final moisture content of the enteric soft capsule shell after vacuum deaeration and drying is about 16%.

The relative percentages of the other components of the enteric soft capsule shell described herein (e.g., gelatin composition, anionic polymer, plasticizers, and optional components such as flavorings, opacifiers, colorants and other excipients as described herein) can be calculated by the relative change in moisture content between the wet enteric soft capsule composition and the dried enteric soft capsule composition as manufactured by the methods described herein (e.g., the percentages of the other components will only increase relative to each other as moisture is removed unless they are fugitive, like ammonia.

In one embodiment described herein, the enteric soft capsule described herein comprises a composition of about 33% gelatin composition; about 3.3% enteric, acid insoluble anionic polymer; about 16% plasticizer; and about 47% solvent.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 2, including all possible iterations of the specified ranges that provide 100% for the total weight percentage, including or excluding the optional, excipients, opacifiers, colorants, and flavorings.

TABLE 2

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer | 8-20 |
| Plasticizer | Glycerol, Triethyl citrate | 15-22 |
| Alkali neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, an enteric soft capsule shell comprises a composition of about 30% film forming polymer; about 10% enteric, acid insoluble polymer; about 20% plasticizer; about 1% alkali neutralizing agent; and about 37% solvent.

In one embodiment, the weight percentage range of total polymer content (i.e., film forming polymer and enteric acid-insoluble polymer) of the enteric soft capsule described herein is about 30% to about 45%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1% to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the weight ratio range of film forming polymer to enteric acid insoluble polymer (film forming: enteric) is about 25:75 ($\approx 0.33$) to about 40:60 ($\approx 0.67$) (i.e., $\approx 0.33$-$0.67$), including all iterations of ratios within the specified range. In one aspect, the ratio of film forming polymer to enteric acid insoluble polymer is about 30:70 ($\approx 0.43$). In another aspect, the ratio of film forming polymer to enteric acid insoluble polymer is about 28:72 ($\approx 0.38$).

In one embodiment, the weight ratio of total plasticizer to film forming polymer is about 20:40 to 21:30 (i.e., $\approx 0.5$-$0.7$), including all iterations of ratios within the specified range. In one aspect, the weight ratio of total plasticizer to film forming polymer is about 20:40 ($\approx 0.5$). In another aspect, the weight ratio of total plasticizer to film forming polymer is about 21:30 ($\approx 0.7$). In another aspect, the weight ratio of total plasticizer to film forming polymer is about 19:29 ($\approx 0.65$). In another aspect, the weight ratio of total plasticizer to film forming polymer is about 19.3:29.2 ($\approx 0.66$).

In one embodiment, the weight ratio of total plasticizer to enteric acid insoluble polymer is about 1:1 to about 2:1 ($\approx 1$-$2$), including all iterations of ratios within the specified range. In one aspect, the weight ratio of total plasticizer to enteric acid insoluble polymer is about 11:10 ($\approx 1.1$). In another aspect, the weight ratio of total plasticizer to enteric acid insoluble polymer is about 14:10 ($\approx 1.4$). In another aspect, the weight ratio of total plasticizer to enteric acid insoluble polymer is about 17:10 ($\approx 1.7$). In another aspect, the weight ratio of total plasticizer to enteric acid insoluble polymer is about 20:10 ($\approx 2$). In another aspect, the weight ratio of total plasticizer to enteric acid insoluble polymer is about 19.3:11.2 ($\approx 1.73$).

In one embodiment, the weight ratio range of total plasticizer to total polymer (film forming and enteric acid insoluble polymer) is about 18:45 to about 20:40 (i.e., $\approx 0.40$-$0.5$), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present in the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 3.

TABLE 3

Exemplary Enteric Soft Capsule Shell Composition

| Component | Percent weight (%) |
|---|---|
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | 4.0-9.0 |
| Total polymer % weight (gelatin + enteric) | 40.4 |
| Gelatin % wt of total polymer (gelatin + enteric) | 72.4 |
| Enteric % wt of total polymer (gelatin + enteric) | 27.6 |
| Ratio of Enteric to Gelatin | 11.2:29.2 (0.38) |
| Total plasticizer % weight (glycerol + triethyl citrate) | 19.3 |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15 |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft capsule composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In one embodiment described herein, soft capsules can be substituted for enteric soft capsules. In one embodiment described herein, the pharmaceutical composition comprises a soft capsule shell comprising a matrix fill further comprising an active pharmaceutical ingredient.

In one embodiment described herein, the soft capsule shell has the composition of Table 4, including all possible iterations of the specified ranges that provide 100% for the total weight percentage, including or excluding the optional colorings, flavorings, or excipients.

TABLE 4

Exemplary Soft Capsule Shell Composition

| Component | Exemplary Component | Composition Range (%) |
|---|---|---|
| Film-forming polymer | Gelatin | 25-50 |
| Plasticizer | Glycerol | 15-25 |
| Solvent | Water | 20-40 |
| Opacifier (optional) | Titanium dioxide | 0.5-1.5 |
| Coloring agent (optional) | Various | 0.05-0.1 |

In one embodiment, the soft capsule shell has the exemplary composition shown in Table 5.

TABLE 5

Exemplary Soft Capsule Shell Composition

| Component | Percent weight (%) |
|---|---|
| Gelatin | 43 |
| Glycerol | 20 |
| Titanium dioxide | 0.7 |
| Coloring agent | 0.1 |
| Water | 36.2 |
| TOTAL | 100% |
| Final pH | 4-7 |
| Ratio total plasticizer to gelatin | 20:43 (0.46:1) |
| Water content in dried soft capsule shell: | 8-15 |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming polymer weight percentage is about 42%. In another aspect, the film-forming polymer weight percentage is about 44%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

Natural colorings can be used to tint the enteric capsule shell. Suitable natural colorings included annatto, betanin, butterfly pea, caramel coloring, chlorophyllin, elderberry juice, lycopene, cochineal, pandan, paprika, turmeric, saffron, and other plant or vegetable colorings.

In some embodiments, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft capsules. In one aspect, enteric soft capsules are made using a rotary die apparatus as described in U.S. Pat. Nos. 5,459,983; 5,146,730; and 6,482,516, each of which are incorporated by reference herein for such teachings.

In another embodiment, the enteric soft capsules described herein have capsule burst strength of about 20 kg to about 60 kg including all integers within the specified range. In one aspect, the enteric soft capsules described herein have a capsule burst strength of about 25 kg. In one aspect, the enteric soft capsules described herein have a capsule burst strength of about 56 kg.

In another embodiment, the enteric soft capsules described herein have high speed cracking strength of about 20 kg to about 60 kg including all integers within the specified range. In one aspect, the enteric soft capsules described herein have a capsule burst strength of about 22 kg. In one aspect, the enteric soft capsules described herein have a capsule burst strength of about 54 kg.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, the pharmaceutical composition comprises an enteric soft capsule shell comprising a matrix fill comprising an active pharmaceutical ingredient.

The enteric soft capsules or soft capsules described herein can contain a matrix fill that is liquid, semi-solid, or solid. Capsules prepared as described herein can contain a hydrophobic solution or suspension, such as vegetable oils or shortening, soybean oils, or waxes, or combinations thereof. The matrix fill can be formulated to prevent interaction with the enteric soft capsule shell components and release the pharmaceutical composition at a specified rate.

The fill can comprise one or more active ingredients and, optionally, one or more pharmaceutically acceptable excipients, colors, or flavorings.

Exemplary lipid or lipophilic liquid or semi-solid lipophilic substances useful for matrix fills include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; and partially hydrogenated oils; bees wax; polyethoxylated bee's wax; paraffin; normal waxes; medium chain medium chain monoglycerides; diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; dicaprylate; monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyldodecanol; myristyl alcohol; isopropyl myristate, isopropyl palmitate, stearic acid, stearyl alcohol, and others known in the art.

Additional solubility enhancing agents useful for the matrix fills include Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 200, polyethylene glycol 400, polyethylene glycol 600, polyethylene glycol 800, polyethylene glycol 1000, polyethylene glycol 2000, polyethylene glycol 3350, Plurol® Oleique CC 497, Povidone K 17, Povidone K 30, and sodium lauryl sulfate.

In one embodiment described herein, the enteric soft capsule or soft capsule matrix has the composition of Table 6, including all possible iterations of the specified ranges that provide 100% for the total weight percentage, including or excluding any optional colorings, flavorings, or excipients.

TABLE 6

Exemplary Soft Capsule Matrix Fill Formulation Ranges

| Ingredient | Composition Range (%) |
|---|---|
| Wetting agent | 0.5-5 |
| Lipophilic liquid | 20-70 |
| Semi-solid lipophilic substance | 2-7 |
| Hydrophilic polysaccharide | 2-10 |
| Hydrophilic polymer | 2-10 |
| Active pharmaceutical ingredient | 20-60 |
| pH | 6.0-9.0 |
| TOTAL | 100% |

In one embodiment described herein, the enteric soft capsule or soft capsule matrix has the composition of Table 7, including all possible iterations of the specified ranges that provide 100% for the total weight percentage, including or excluding any optional colorings, flavorings, or excipients.

TABLE 7

Exemplary Soft Capsule Matrix Fill Formulation Ranges

| Ingredient | Composition Range (%) |
|---|---|
| Solubility enhancing agent | 10-85 |
| Solubilizing Plasticizer | 2.5-10 |
| Water | 2.5-20 |
| Active pharmaceutical ingredient | 5-80 |
| pH | 6.0-9.0 |
| TOTAL | 100% |

In one embodiment described herein, the matrix fill of the pharmaceutical composition comprises a wetting agent comprising from about 0.5% to about 5% of the matrix fill mass including all iterations of integers within the specified range. In one aspect, the wetting agent comprises about 0.5% of the matrix fill mass. In another aspect, the wetting agent comprises about 2% of the matrix fill mass. In another aspect, the wetting agent comprises about 3% of the matrix fill mass. In one aspect, the wetting agent comprises about 4% of the matrix fill mass. In one aspect, the wetting agent comprises lecithin.

In one embodiment described herein, the matrix fill of the pharmaceutical composition comprises one or more lipophilic liquids comprising from about 20% to about 70% of the matrix fill mass including all iterations of integers within the specified range. In one aspect, the one or more lipophilic liquids comprises about 26% of the matrix fill mass. In another aspect, the one or more lipophilic liquids comprises about 45% of the matrix fill mass. In another aspect, the one or more lipophilic liquids comprises about 55% of the matrix fill mass. In another aspect, the one or more lipophilic liquids comprises about 65% of the matrix fill mass. In another aspect, the one or more lipophilic liquids comprises vegetable oil and/or soybean oil.

In one embodiment described herein, the matrix fill of the pharmaceutical composition comprises a semi-solid lipophilic substance comprising from about 2% to about 7% of the matrix fill mass including all iterations of integers within the specified range. In one aspect, the semi-solid lipophilic substance comprises about 2% of the matrix fill mass. In another aspect, the semi-solid lipophilic substance comprises about 3% of the matrix fill mass. In another aspect, the semi-solid lipophilic substance comprises about 4% of the matrix fill mass. In another aspect, the semi-solid lipophilic substance comprises about 6% of the matrix fill mass. In another aspect, the semi-solid lipophilic substance comprises bee's wax.

In one embodiment described herein, the matrix fill of the pharmaceutical composition comprises a hydrophilic polysaccharide comprising from about 2% to about 10% of the matrix fill mass including all iterations of integers within the specified range. In one aspect, the hydrophilic polysaccharide comprises about 2% of the matrix fill mass. In another aspect, the hydrophilic polysaccharide comprises about 4% of the matrix fill mass. In another aspect, the hydrophilic polysaccharide comprises about 7% of the matrix fill mass. In another aspect, the hydrophilic polysaccharide comprises about 9% of the matrix fill mass. In another aspect, the hydrophilic polysaccharide comprises chitosan.

In one embodiment described herein, the matrix fill of the pharmaceutical composition comprises a hydrophilic polymer comprising from about 2% to about 10% of the matrix fill mass including all iterations of integers within the specified range. In one aspect, the hydrophilic polymer comprises about 2% of the matrix fill mass. In one aspect, the hydrophilic polymer comprises about 4% of the matrix fill mass. In one aspect, the hydrophilic polymer comprises about 7% of the matrix fill mass. In one aspect, the hydrophilic polymer comprises about 9% of the matrix fill mass. In one aspect, the hydrophilic polymer comprises Carbopol® 971.

In one embodiment described herein, the matrix fill of the pharmaceutical composition comprises a wetting agent of about 1.5%, a mixture of two lipophilic liquids of about 65%, a semi-solid lipophilic substance of about 3%, a hydrophilic polysaccharide of about 5%, a hydrophilic polymer of about 5%, and an active pharmaceutical ingredient of about 6% to about 20% including all iterations of integers within the specified range. In one aspect, the matrix fill comprises an active pharmaceutical ingredient of about 6%. In another aspect, the matrix fill comprises an active pharmaceutical ingredient of about 20%.

In one embodiment described herein, the weight ratio range of one or more lipophilic liquids to the semi-solid substance is about 5:1 to about 25 to 1, including all ratios within the specified range. In one aspect, the weight ratio of one or more lipophilic liquids to the semi-solid substance is about 22 to 1.

In one embodiment described herein, the weight ratio range of hydrophilic components (e.g., hydrophilic polysaccharide and hydrophilic synthetic) to lipophilic components (e.g., lipophilic liquid and lipophilic semi-solid substance) is about 1:30 to about 1:2, including all ratios within the specified range. In one aspect, the weight ratio of one or more hydrophilic polymers to lipophilic is about 1:7.

In one embodiment described herein, the weight ratio range of wetting agent to hydrophilic and lipophilic components is about 1:30 to about 1:2, including all ratios within the specified range. In one aspect, the weight ratio of wetting agent to hydrophilic and lipophilic is about 1:50.

In one embodiment described herein, the matrix fill of the pharmaceutical composition comprises a solubility enhancing agent comprising from about 10% to about 35% of the matrix fill mass including all iterations of integers within the specified range. In one aspect, the solubility enhancing agent comprises about 10% of the matrix fill mass. In another aspect, the solubility enhancing agent comprises about 20% of the matrix fill mass. In another aspect, the solubility enhancing agent comprises about 35% of the matrix fill mass.

In another embodiment described herein, the solubility enhancing agent comprises from about 45% to about 85% of the matrix fill mass including all iterations of integers within the specified range. In one aspect, the solubility enhancing agent comprises about 45% of the matrix fill mass. In another aspect, the solubility enhancing agent comprises about 65% of the matrix fill mass. In another aspect, the solubility enhancing agent comprises about 80% of the matrix fill mass.

In one embodiment, the solubility enhancing agent increases the solubility of active pharmaceutical ingredients described herein. In one aspect, the solubility enhancing agent increases the solubility of diclofenac potassium. In another aspect, the solubility enhancing agent comprises polyethylene glycol 600. In another aspect, the solubility enhancing agent comprises polyethylene glycol 400. In one aspect, polyethylene glycol 600 was unexpectedly superior to polyethylene glycol 400 as a solubility enhancing agent.

In one embodiment described herein, the matrix fill of the pharmaceutical composition comprises a solubilizing plasticizer comprising from about 2.5% to about 10% of the matrix fill mass including all iterations of integers within the specified range. In one aspect, the solubilizing plasticizer comprises about 3% of the matrix fill mass. In another aspect, the solubilizing plasticizer comprises about 5% of the matrix fill mass. In another aspect, the solubilizing plasticizer comprises about 10% of the matrix fill mass.

In one embodiment, the solubilizing plasticizer comprises glycerol. In another embodiment, the solubilizing plasticizer comprises propylene glycol. In another embodiment, propylene glycol is superior to glycerol as a solubilizing plasticizer.

In one embodiment described herein, the matrix fill of the pharmaceutical composition comprises a solubility enhancing agent of about 80%, a mixture of two lipophilic liquids of about 65%, a solubilizing plasticizer of about 5%, water content of about 5%, and an active pharmaceutical ingredient of about 11% to about 40% including all iterations of integers within the specified range. In one aspect, the matrix fill comprises an active pharmaceutical ingredient of about 6%. In another aspect, the matrix fill comprises an active pharmaceutical ingredient of about 11%. In another aspect, the matrix fill comprises an active pharmaceutical ingredient of about 30%. In another aspect, the matrix fill comprises an active pharmaceutical ingredient of about 35%.

In one embodiment, the matrix fill is comprised of the soft capsule shells described herein. Without being bound by any theory, it is believed that water migrates from the soft capsule shells described herein into the matrix fill described herein. In another aspect, the water content of the matrix fill is increased by about 3% to about 15% by the migration of water from the shell to the fill.

In one embodiment described herein, the weight ratio range of solubility enhancing agent to solubilizing plasticizer is about 2:1 to about 40:1, including all ratios within the specified range. In one aspect, the weight ratio of solubility enhancing agent to solubilizing plasticizer is about 16:1.

In one embodiment described herein, the weight ratio range of solubility enhancing agent to water is about 2:1 to about 40:1, including all ratios within the specified range. In one aspect, the weight ratio of solubility enhancing agent to water is about 16:1.

In one embodiment described herein, the weight ratio range of solubilizing plasticizer to water is about 1:2 to about 2:1, including all ratios within the specified range. In one aspect, the weight ratio of wetting agent to hydrophilic and lipophilic is about 1:1.

In one embodiment described herein, the weight ratio range of active pharmaceutical ingredient to solubility enhancing agent is about 1:17 to about 8:1, including all ratios within the specified range. In one aspect, the weight ratio of active pharmaceutical ingredient to hydrophilic components is about 1:7. In another embodiment described herein, the weight ratio range of active pharmaceutical ingredient to solubilizing plasticizer is about 1:1 to about 16:1, including all ratios within the specified range. In one aspect, the weight ratio of active pharmaceutical ingredient to lipophilic components is about 2:1. In another embodiment described herein, the weight ratio range of active pharmaceutical ingredient to water is about 1:1 to about 16:1, including all ratios within the specified range. In one aspect, the weight ratio of active pharmaceutical ingredient to wetting agent is about 2:1.

The matrix fill can optionally include one or more pharmaceutically acceptable excipients. Examples of pharmaceutically acceptable excipients include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinyl pyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), and PLURONICS™ (BASF; Florham Park, N.J.). Diluents commonly used in the art can also be encapsulated within the shell, including water or other solvents, solubilizing agents, and emulsifiers, as for example, ethyl alcohol, isopropyl alcohol, ethyl carbonate, ethyl acetate, benzyl alcohol, benzyl benzoate, 1,3-butylene glycol, dimethylformamide, oils, in particular, cottonseed oil, groundnut oil, corn germ oil, olive oil, castor oil, sesame oil, glycerol, tetrahydrofurfuryl alcohol, and fatty acid esters of sorbitan, and mixtures of these substances.

Additional pharmaceutical excipients useful for matrix fills include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Alkalizing agents (ammonia solution, ammonium carbonate, diethanolamine, diisopropanolamine, potassium hydroxide, sodium bicarbonate, sodium borate, sodium carbonate, sodium hydroxide, trolamine); Antifoaming agents (dimethicone, simethicone); Antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, sorbitol); Plasticizers (e.g., castor oil, diacetylated monoglycerides, diethyl phthalate, glycerin, mono- and di-acetylated monoglycerides, propylene glycol, triacetin, triethyl citrate); Polymers (e.g., cellulose acetate, alkyl celluloses, hydroxyalkyl, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

In one embodiment, the matrix fill can include a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with *Physical Pharmacy: Physical Chemical Principles in the Pharmaceutical Sciences,* 4$^{th}$ ed., 371-373, A. Martin, Ed., Lippincott Williams & Wilkins, Philadelphia (1993), which is incorporated by reference herein for such teachings.

In one embodiment, the matrix fill may include one or more hydrophilic carriers. Examples of hydrophilic carriers are all natural, synthetic, or semi-synthetic products, which can be defined as aqueous carriers not mixable or only partially mixable with oil. All components can be used alone or if possible in mixtures with different percentages. Among aqueous components which can be used as a dispersing phase or also as a dispersed phase.

Examples of aqueous solutions of hydrophilic polymers, which are hydrosoluble or hydrodispersable of various nature, such as polyethylenglycol, polyvinyl pyrrolidone, polyacrylic acids and derivatives, such as Carbopol® 971, polymethacrylic acids polyoxyethylenepolyoxypropylene copolymers (for example Poloxamer®, Lutrol™), hydrophilic polysaccharides of various nature, for example dextran, xanthan, scleroglucan, arabic gum, guar gum, chitosan, cellulose and starch derivatives.

In one embodiment, the matrix fill can include a neutralizing agent. Without being bound to any theory, the neutralizing agent is thought to stabilize the active pharmaceutical ingredient in the matrix fill by preventing hydrolysis. In addition, without being bound by any theory, it is also thought that the neutralizing agent stabilizes the enteric soft capsule shell by forming salts with the methylacrylate moieties from the enteric soft capsule shell. In one aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, esters or salts thereof, or combinations thereof.

In one embodiment, the matrix fill can include a hydrophilic internal phase and a lipid or lipophilic external phase. The internal phase of the matrix fill can include a plasticizer, such as propylene glycol, or a solubility enhancing agent, such as polyethylene glycol of molecular mass ranging from about 200 g/mol to about 8000 g/mol. In another embodiment, the internal phase can include hydroalcoholic solutions of cellulose derivatives, hydrophilic polymers, polyacrylates, polyacrylic acids and derivatives (e.g., Carbopol™) polyvinyl polymers, chitosan or combinations thereof.

In another embodiment, the internal phase of the matrix fill can include polymers, such as methylcellulose, hydroxypropylmethylcellulose, polymethylmethacrylate, or polyvinylpyrrolidone (PVP). The internal phase of the matrix fill can also be structured. A "structured" internal phase of the matrix fill, as used herein, means a solid, semisolid, or a gel whose shape is relatively stable and does not usually aggregate to form a large globule. A structured internal phase of the matrix fill therefore provides controlled drug release and stabilizes the physical state of the matrix. Without being bound by any theory, it is believed that the structured nature of the matrix fill impedes solvation and/or diffusion of the active pharmaceutical ingredient out of the matrix fill. In another embodiment, the external phase of the matrix fill can include a vegetable oil, hydrogenated vegetable oil (including shortening), fatty acids, fatty acid esters, wax, bee's wax, soybean oil, or a combination thereof. In another embodiment, an active pharmaceutical ingredient can be dispersed in the internal phase of the matrix fill as a suspension form.

In one embodiment, the matrix fill is a liquid (e.g., a solution, suspension, or dispersion) or a semisolid (e.g., a paste or gel). In one aspect, the active pharmaceutical ingredient can be innately a liquid or semisolid. In another aspect, the active ingredient can be prepared as a liquid or semisolid by, for example, by dissolving or otherwise mixing an active ingredient and optionally one or more pharmaceutical adjuvants in a carrier, such as, for example, water, saline, aqueous dextrose, glycerol, glycols (e.g., propylene glycol), ethanol, fatty acids, glycerides, oils, sterols, phospholipids, and the like, to thereby form a solution.

In one embodiment described herein, the matrix fill comprises a lipid or lipophilic vehicle that provides a suspension of an active pharmaceutical ingredient having defined sizes. In one aspect, an enteric soft capsule comprising a suspension of an active pharmaceutical ingredient provides delayed release delivery of the active pharmaceutical ingredient.

In one embodiment described herein, the pharmaceutical composition provides matrix fills for an active pharmaceutical ingredient, or derivatives thereof, based on lipids or lipophilic materials. The described matrices have a hydrophobic (lipophilic) surface in contact with a hydrophilic soft enteric capsule shell to minimize any potential shell-fill interactions, such as when the enteric soft capsules are filled with hydrophilic materials.

Examples of active pharmaceutical ingredients that can be included comprise agents classified as, for example, an adrenocortical steroid, adrenocortical suppressant, aldosterone antagonist, amino acid, anabolic steroid, androgen, antagonist, anthelmintic, anti-acne agent, anti-adrenergic, anti-allergic, anti-amebic, anti-androgen, anti-anemic, anti-anginal, anti-arthritic, anti-asthmatic, anti-atherosclerotic, antibacterial, anticholelithic, anticholelithogenic, anticholinergic, anticoagulant, anticoccidal, antidiabetic, antidiarrheal, antidiuretic, antidote, anti-estrogen, antifibrinolytic, antifungal, antiglaucoma agent, antihemophilic, antihemorrhagic, antihistamine, antihyperlipidemic, antihyperlipoproteinemic, antihypertensive, antihypotensive, anti-infective, anti-infective, anti-inflammatory, antikeratinizing agent, antimalarial, antimicrobial, antimitotic, antimycotic, antineoplastic, antineutropenic, antiparasitic, antiperistaltic, antipneumocystic, antiproliferative, antiprostatic hypertrophy, antiprotozoal, antipruritic, antipsoriatic, antirheumatic, antischistosomal, anti seborrheic, anti secretory, antispasmodic, antithrombotic, antitussive, anti-ulcerative, anti-urolithic, antiviral, appetite suppressant, benign prostatic hyperplasia therapy agent, bone resorption inhibitor, bronchodilator, carbonic anhydrase inhibitor, cardiac depressant, cardioprotectant, cardiotonic, cardiovascular agent, choleretic, cholinergic, cholinergic agonist, cholinesterase deactivator, coccidiostat, contrasting agent, diagnostic aid, diuretic, ectoparasiticide, enzyme inhibitor, estrogen, fibrinolytic, free oxygen radical scavenger, glucocorticoid, gonad-stimulating principle, hair growth stimulant, hemostatic, hormone, hypocholesterolemic, hypoglycemic, hypolipidemic, hypotensive, imaging agent, immunizing agent, immunomodulator, immunoregulator, immunostimulant, immunosuppressant, impotence therapy adjunct, inhibitor, keratolytic, LHRH agonist, liver disorder treatment, luteolysin, mucolytic, mydriatic, nasal decongestant, neuromuscular blocking agent, non-hormonal sterol derivative, nonsteroidal anti-inflammatory drugs, oxytocic, plasminogen activator, platelet activating factor antagonist, platelet aggregation inhibitor, potentiator, progestin, prostaglandin, prostate growth inhibitor, prothyrotropin, radioactive agent, regulator, relaxant, repartitioning agent, scabicide, sclerosing agent, selective adenosine A1 antagonist, steroid, suppressant, symptomatic multiple sclerosis, synergist, thyroid hormone, thyroid inhibitor, thyromimetic, amyotrophic lateral sclerosis agents, Paget's disease agents, unstable angina agents, uricosuric, vasoconstrictor, vasodilator, vulnerary, wound healing agent, and xanthine oxidase inhibitor. Further examples of suitable pharmaceutical ingredients include those as listed in the Merck Index (13$^{th}$ Edition, Wiley, 2001), The United States Pharmacopeia-National Formulary (USP-NF), and the FDA's Orange book, which are each incorporated by reference herein for their teachings of pharmaceutically active ingredients.

Examples of nutraceuticals include, but are not limited to, amino acids, terpenoids (e.g., carotenoid terpenoids and non-carotenoid terpenoids), herbal supplements, homeopathic supplements, glandular supplements, polyphenolics, flavonoid polyphenolics, phenolic acids, curcumin, resveratrol, lignans, glucosinolates, isothiocyanates, indoles, thiosulfinates, phytosterols, anthraquinones, capsaicin, piperine, chlorophyll, betaine, oxalic acid, acetyl-L-carnitine, allantoin, androstenediol, androstendione, betaine (trimethylglycine), caffeine, calcium pyruvate (pyruvic acid), carnitine, carnosine, carotene, carotenoid, choline, chlorogenic acid, cholic acid, chondroitin sulfate, chondroitin sulfate, cholestan, chrysin, coenzyme Q10, conjugated linoleic acid, corosolic acid, creatine, dehydroepiandrosterone, dichlorophen, diindolymethane, dimethylglycine, dimercapto succinic acid, ebselen, ellagic acid, enzymes, fisetin, formononetin, glucaric acid (glucarate), glucosamine (HCl or sulfate), glucosamine (N-acetyl), glutathione, hesperidine, hydroxy-3-methylbutyric acid, 5-hydroxytryptophan, indole-3-carbinol, inositol, isothiocyanates, linolenic acid-gamma, lipoic acid (alpha), melatonin, methylsulfonylmethane, minerals, naringin, pancreatin, para-aminobenzoic acid, paraben (methyl or propyl), phenolics, phosphatidylcholine, phosphatidylserine, phospholipids, phytosterols, progesterone, pregnenolone, omega-3 fatty acids, quercetin, resveratrol, D-ribose, rutin, S-adenosylmethionine, salicylic acid, sulforaphane, tartaric acid, taxifolin, tetrahydropalmatine, theophyline, theobromine, tigogenin, troxerutin, tryptophan, tocotrienol (alpha, beta, and gamma), zeaxanthin, gingko biloba, ginger, cat's claw, hypericum, aloe vera, evening primrose, garlic, capsicum, dong quai, ginseng, feverfew, fenugreek, echinacea, green tea, marshmallow, saw palmetto, tea tree oil, fish oil, psyllium, kava-kava, licorice root, mahonia aquifolium, hawthorne, yohimbe, tumeric, witch Hazel, valerian, mistletoe, bilberry, bee pollen, peppermint oil, beta-carotene, genistein, lutein, lycopene, the polyphenols, and the like. Further examples of suitable nutraceuticals include those listed in *Handbook of Nutraceuticals and Functional Foods*, Robert E. C. Wildman, Ed., CRC Press (2001), which is incorporated by reference herein for the teachings related to nutraceuticals.

Examples of non-steroidal anti-inflammatory drugs (NSAID) comprise aceclofenac, acemetacin, aloxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, tolmetin, or valdecoxib.

Other useful pharmaceutical ingredients or nutraceuticals that can be included as an active ingredient include fish oils, egg oils, squid oils, krill oils, nut oils, seed oils; soy oils, avocado oils, seabuckthorn seed or berry oils, clary sage seed oils, algal oils, flaxseed oils, sacha ichi oils, echium oils, hemp oils, omega-3 fatty acids, polyunsaturated omega-3 fatty acids, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA), clupanodonic acid), docosahexaenoic acid (DHA, cervonic acid), tetracosapentaenoic acid, tetracosahexaenoic acid (nisinic acid), and free acids, etheyl esters, or other esters or salts thereof. In one aspect, the pharmaceutical ingredient is a highly purified omega-3 fatty acid, ester, or salt thereof.

Vitamins are nutraceuticals or pharmaceutical ingredients that include organic substances that are typically considered essential for the normal growth and activity of a subject (e.g., a human or non-human animal patient to whom the composition is to be administered). Examples of vitamins include, but are not limited to vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, and para-aminobenzoic acid.

Vitamins can also include naturally occurring inorganic substances that are typically considered essential for the normal growth and activity of a subject (e.g., a human or non-human animal patient to whom the composition is to be administered). Examples of minerals include, but are not limited to, boron, calcium, chromium, copper, iron, magnesium, manganese, molybdenum, nickel, phosphorus, selenium, silicon, tin, vanadium, and zinc.

In one embodiment described herein, an active pharmaceutical ingredient is the only active ingredient in the pharmaceutical composition. In another embodiment, the active ingredient or drug can be an active pharmaceutical ingredient, derivatives thereof, or combinations thereof.

In one embodiment, the pharmaceutical compositions as described herein are suitable for use for water soluble as well as slightly soluble or insoluble active drug substances.

In another embodiment, the pharmaceutical compositions described herein may comprise pharmaceutically acceptable salts of any of the above mentioned active drug substances. The term "pharmaceutically acceptable salts" of an active pharmaceutical ingredient includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, the active pharmaceutical ingredient may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the active pharmaceutical ingredient may be in any of its crystalline, polymorphous, semicrystalline, amorphous or polyamorphous forms or mixtures thereof.

In one embodiment described herein, the ratio of the active ingredient or drug to the total matrix fill, e.g., matrix fill ingredient(s) and active pharmaceutical ingredient(s), can be from about 1:50 to about 1:1 by weight, including all ratios in the specified range. In another embodiment described herein, the active ingredient to total matrix fill ratio can also be from about 1:16 to about 1:1 by weight, including all ratios in the specified range. The active ingredient to total matrix fill ratio can also be about 1:16; about 1:9; about 1:3; about 1:2; or about 1:1 including all ratios in the specified range.

In one embodiment described herein, the active ingredient or drug comprises from about 5% to about 80% of the matrix fill mass including all iterations of integers within the specified range. In one aspect described herein, the active ingredient or drug comprises about 80% of the matrix fill mass. In another aspect, the active ingredient or drug comprises about 60% of the matrix fill mass. In another aspect, the active ingredient or drug comprises about 40% of the matrix fill mass. In another aspect, the active ingredient or drug comprises about 6% of the matrix fill mass.

In another embodiment described herein, the active ingredient or drug comprises about 80%, about 70%, about 60%, about 50%, about 40%, about 30%, about 20%, about 15%, about 10%, about 5%, about 2%, or about 1% of the matrix fill mass.

In one embodiment described herein, the weight ratio range of the active pharmaceutical ingredient to the matrix fill mass is about 1:20 to about 10:1. In one aspect, the weight ratio of the active pharmaceutical ingredient to the matrix fill mass is about 1:3. In another aspect, the weight ratio of the active pharmaceutical ingredient to the matrix fill mass is about 1:9. In another aspect, the weight ratio of the active pharmaceutical ingredient to the matrix fill mass is about 1:17.

In one embodiment, the composition described herein can provide a dosage of an active ingredient for administration. The dosage form can be administered, for example, to a subject, or a subject in need thereof. In one aspect, the subject may be a mammal, or a mammal in need thereof. In another aspect, the dosage form can be administered, for example, to a human or a human in need thereof. In another aspect, the human subject or a human subject in need thereof is a medical patient.

In one embodiment, the pharmaceutical composition described herein, comprises an active pharmaceutical ingredient of about 10 mg to about 500 mg.

In one embodiment, the pharmaceutical composition described herein, comprises an active pharmaceutical ingredient of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, or even more.

In one embodiment, the pharmaceutical composition described herein, comprises an active pharmaceutical ingredient of about 20 mg to about 250 mg including all iterations of integers within the specified range.

In another embodiment, the pharmaceutical composition described herein, comprises an active pharmaceutical ingredient in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, or about 240 mg to about 250 mg, including all iterations of integers within the specified ranges above.

In one embodiment described herein, the soft capsules described herein comprise an active pharmaceutical ingredient comprising diclofenac or a pharmaceutically acceptable salt form thereof, including but not limited to diclofenac sodium, diclofenac potassium, or diclofenac hydrochloride. In another embodiment, diclofenac is present in its free acid form. As used herein, "diclofenac" refers to all possible salt forms of the active pharmaceutical ingredient if a particular salt is not specified.

In one embodiment described herein, the dose of diclofenac is about 10 mg to about 500 mg, including all integers within the specified range. In one aspect, the dose of diclofenac is about 10 mg. In another aspect, the dose of diclofenac is about 12.5 mg. In another aspect, the dose of diclofenac is about 25 mg. In another aspect, the dose of diclofenac is about 50 mg. In another aspect, the dose of diclofenac is about 75 mg. In another aspect, the dose of diclofenac is about 100 mg. In another aspect, the dose of diclofenac is about 125 mg. In another aspect, the dose of diclofenac is about 150 mg. In another aspect, the dose of diclofenac is about 175 mg. In another aspect, the dose of diclofenac is about 200 mg. In another aspect, the dose of diclofenac is about 225 mg. In another aspect, the dose of diclofenac is about 250 mg. In another aspect, the dose of diclofenac is about 300 mg. In another aspect, the dose of diclofenac is about 350 mg. In another aspect, the dose of diclofenac is about 400 mg. In another aspect, the dose of diclofenac is about 450 mg. In another aspect, the dose of diclofenac is about 500 mg.

The concentration of the active pharmaceutical ingredient in the pharmaceutical composition depends on the specific active pharmaceutical ingredient, the disease to be treated, the condition of the patient, the age, and gender of the patient, etc. The active pharmaceutical ingredient may be a well-known active pharmaceutical ingredient and a person having ordinary skill in the art will be able to find information as to the dosage of each active drug substance and, accordingly, will know how to determine the amount of each active drug substance in the pharmaceutical composition.

In one aspect described herein, the dose of diclofenac is 12.5 mg. In another aspect, the dose of diclofenac is 20 mg. In another aspect, the dose of diclofenac is 25 mg. In another aspect, the dose of diclofenac is 50 mg. In another aspect, the dose of diclofenac is 75 mg. In another aspect, the dose of diclofenac is 100 mg. In another aspect, the dose of diclofenac is 150 mg. In another aspect, the dose of diclofenac is 200 mg. In another aspect, the dose of diclofenac is 250 mg. In another aspect, the dose of diclofenac is 300 mg. In another aspect, the dose of diclofenac is 350 mg. In another aspect, the dose of diclofenac is 400 mg. In another aspect, the dose of diclofenac is 450 mg. In another aspect, the dose of diclofenac is 500 mg.

In one embodiment, the dosage can contain an amount of diclofenac effective for treatment, amelioration, prophylaxis, or reducing the onset of or symptoms of mild, moderate, or severe pain stemming from arthritis.

In another embodiment, the dosage can contain an amount of diclofenac effective for treatment, amelioration, prophylaxis, or reducing the onset of or symptoms of mild, moderate, or severe pain stemming from tendonitis.

In another embodiment, the dosage can contain an amount of diclofenac effective for treatment, amelioration, prophylaxis, or reducing the onset of or symptoms of mild, moderate, or severe pain stemming from bursitis.

In another embodiment, the dosage can contain an amount of diclofenac effective for treatment, amelioration, prophylaxis, or reducing the onset of or symptoms of mild, moderate, or severe pain stemming from chronic neuropathies.

In another embodiment, the dosage can contain an amount of diclofenac effective for treatment, amelioration, prophylaxis, or reducing the onset of or symptoms of mild, moderate, or severe pain stemming from shingles.

In another embodiment, the dosage can contain an amount of diclofenac effective for treatment, amelioration, prophylaxis, or reducing the onset of or symptoms of mild, moderate, or severe pain stemming from chronic sports injuries.

In another embodiment, the dosage can contain an amount of diclofenac effective for treatment, amelioration, prophylaxis, or reducing the onset of or symptoms of mild, moderate, or severe pain stemming from chronic malignancies and/or cancer.

In another embodiment, the dosage can contain an amount of diclofenac effective for treatment, amelioration, prophylaxis, or reducing the onset of or symptoms of mild, moderate, or severe pain stemming from chronic radiculopathy.

In another embodiment, the dosage can contain an amount of diclofenac effective for treatment, amelioration, prophylaxis, or reducing the onset of or symptoms of mild, moderate, or severe pain stemming from chronic sciatica.

In another embodiment, the dosage can contain an amount of diclofenac effective for treatment, amelioration, prophylaxis, or reducing the onset of or symptoms of pain associated with kidney stones.

In another embodiment, the dosage can contain an amount of diclofenac effective for treatment, amelioration, prophylaxis, or reducing the onset of or symptoms of menstrual pain.

In another embodiment, the dosage can contain an amount of diclofenac effective for treatment, amelioration, prophylaxis, or reducing the onset of or symptoms of pain associated with endometriosis.

In one embodiment, the dosage can contain an amount of diclofenac effective for treatment, amelioration, prophylaxis, or reducing the onset of or symptoms of inflammation. In another embodiment, the dosage can contain an amount of diclofenac effective for treatment, amelioration, prophylaxis, or reducing the onset of or symptoms of mild, moderate, or severe fever.

In another embodiment, the dosage can contain an amount of diclofenac effective for treatment, amelioration, prophylaxis, or reducing the onset of or symptoms of dysmenorrhea.

In another embodiment, the dosage can contain an amount of diclofenac effective for treatment, amelioration, prophylaxis, or reducing the onset of or symptoms of acute migraines.

In another embodiment, the dosage can contain an amount of diclofenac effective for treatment, amelioration, prophylaxis, or reducing the onset of or symptoms of osteoarthritis.

In another embodiment, the dosage can contain an amount of diclofenac effective for treatment, amelioration, prophylaxis, or reducing the onset of or symptoms of rheumatoid arthritis.

In another embodiment, the dosage can contain an amount of diclofenac effective for treatment, amelioration, prophylaxis, or reducing the onset of or symptoms of ankylosing spondylitis.

In another embodiment, the dosage can contain an amount of diclofenac effective for treatment, amelioration, prophylaxis, or reducing the onset of or symptoms of spondylarthritis.

In another embodiment, the dosage can contain an amount of diclofenac effective for treatment, amelioration, prophylaxis, or reducing the onset of or symptoms of gout.

The exact mechanism of action of diclofenac is not entirely known, but without being bound to any theory, the primary mechanism thought to be responsible for diclofenac's anti-inflammatory, antipyretic, and analgesic action is the inhibition of prostaglandin synthesis by inhibition of cyclooxygenase (COX). In addition, diclofenac appears to exhibit bacteriostatic activity by inhibiting bacterial DNA synthesis. See, Current Medical Research and Opinion (2010) 26 (7): 1715-1731 and International Journal of Antimicrobial Agents (2000) 14 (3): 249-251).

In one embodiment, the total dosage of diclofenac administered in a 24-hour period is about 20 mg to about 1000 mg per 24-hour period including all iterations of integers within the specified range. In another embodiment, the total dosage of diclofenac administered in a 24-hour period is about 50 mg to about 250 mg per 24-hour period including all iterations of integers within the specified range. In one aspect, the total dosage of diclofenac administered in a 24-hour period is about 50 mg. In another aspect, the total dosage of diclofenac administered in a 24-hour period is about 100 mg. In another aspect, the total dosage of diclofenac administered in a 24-hour period is about 150 mg. In another aspect, the total dosage of diclofenac administered in a 24-hour period is about 200 mg. In another aspect, the total dosage of diclofenac administered in a 24-hour period is about 250 mg. In another aspect, the total dosage of diclofenac administered in a 24-hour period is about 500 mg. In another aspect, the total dosage of diclofenac administered in a 24-hour period is about 750 mg. In another aspect, the total dosage of diclofenac administered in a 24-hour period is about 1000 mg.

In another embodiment, the total dosage of diclofenac administered in a 24-hour period is about 100 mg to about 150 mg and is effective for the treatment of osteoarthritis administered in equal daily doses (i.e., 25 mg 4 or 5 times daily; 50 mg 2 or 3 times daily; 75 mg 2 times daily; 100 or 150 mg 1 time daily; or combinations thereof to reach a desired therapeutic efficacy).

In another embodiment, the total dosage of diclofenac administered in a 24-hour period is about 150 mg to about 200 mg and is effective for the treatment of rheumatoid arthritis administered in equal daily doses (i.e., 25 mg 6 or 8 times daily; 50 mg 3 or 4 times daily; 75 mg 2 times daily; 100 mg 2 times daily; 150 mg 1 times diallyl; or combinations thereof to reach a therapeutic efficacy).

In another embodiment, the total dosage of diclofenac administered in a 24-hour period is about 100 mg to about 125 mg and is effective for the treatment of ankylosing spondylitis administered in equal daily doses (i.e., 25 mg 4 or 5 times daily; 50 mg 2 times daily; 100 mg 1 time daily; or combinations thereof to reach a therapeutic efficacy).

The dosage form can be administered, for example, 1×, 2×, 3×, 4×, 5×, 6×, 7×, or 8×, per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, or even longer. One or more dosage forms can be administered until the patient, subject, mammal, mammal in need thereof, human, or human in need thereof, does not require treatment, prophylaxis, or amelioration of any disease or condition such as, for example, pain.

In another embodiment described herein, the total mass of the matrix fill of the pharmaceutical composition described herein that comprises an active pharmaceutical ingredient described herein is from about 50 mg to about 500 mg. In one aspect, the total mass of the matrix fill mass is about 80 mg. In another aspect, the total mass of the matrix fill mass is about 220 mg. In one aspect, the total mass of the matrix fill mass is about 420 mg. In another aspect, the total mass of the matrix fill mass is about 220 mg. In another aspect, the total mass of the matrix fill mass is about 500 mg.

Described herein are methods for manufacturing matrix fills comprising an active pharmaceutical ingredient in a controlled release enteric soft capsule in the form of a suspension, where part or all of the active pharmaceutical ingredient is suspended within the matrix fill. Also provided are compositions and formulations where the active pharmaceutical ingredient is incorporated in a one-phase matrix fill. A one-phase matrix fill can be comprised of a homogeneous mixture of lipid or lipophilic materials.

In one embodiment, a matrix fill as described herein can be manufactured by adding the specified amounts of wetting agent, lipophilic liquids and semi-solid lipophilic substance and melting said ingredients at 65° C. under agitation. In a next step, the required amount of hydrophilic polymer, hydrophilic polysaccharide, and active pharmaceutical ingredient is mixed, homogenized, and de-aired resulting in a matrix fill composition comprising an active pharmaceutical ingredient. In one aspect, the described matrix fill is encapsulated in a soft capsule utilizing standard rotary die encapsulation methods. Suitable active ingredients can include, for example, active pharmaceutical ingredients (e.g., therapeutic agents, prophylactic agents, and diagnostic agents), nutraceuticals, vitamins, minerals, and combinations thereof.

Another embodiment described herein is a method for treating, ameliorating the symptoms of, or delaying the onset of a medical condition by providing a subject in need thereof with a pharmaceutical composition comprising an enteric soft capsule, as described herein, comprising a pharmaceutical ingredient or ingredients. As used herein, a medical condition can comprise any actual or suspected disease, disorder, or condition that a subject may seek medical care therefor. One embodiment described herein is method of treating, ameliorating the symptoms of, or delaying the onset of a medical condition of includes administering a pharmaceutical ingredient having a desired therapeutic or biological activity or suspected of having a desired therapeutic or biological activity in a subject in need thereof.

In one embodiment described herein, the enteric soft capsule shell and matrix fills described herein prevent or reduce the onset of esophageal irritation, esophageal erosion, gastric irritation, gastric reflux, peptic ulcers, stomach bleeding, or ulceration from non-steroidal anti-inflammatory drug administration. In one aspect, the enteric soft capsule shell and matrix fills described herein prevent or reduce the onset of esophageal irritation, esophageal erosion, gastric irritation, gastric reflux, peptic ulcers, stomach bleeding, or ulceration from diclofenac administration. Without being bound to any theory, it is believed that the enteric soft capsule shells are able to prevent, delay, or reduce the onset of esophageal irritation, esophageal erosion, gastric irritation, gastric reflux, peptic ulcers by being easily and quickly swallowed and also by restricting the release of the non-steroidal anti-inflammatory drug after ingestion to the intestine. Non-steroidal anti-inflammatory drugs can inhibit prostaglandin synthesis locally in the stomach, which can increase stomach acidity and lead to esophageal damage and stomach ulceration.

In one embodiment described herein, the soft capsules described herein comprise a matrix fill having controlled, delayed, or extended release properties. Such controlled or extended release matrix fills are described in International Patent Application Publication No. WO 2005/009409 and U.S. Patent Application Publication No. US 2006/0115527, both of which are incorporated by reference herein for such teachings. In one aspect, the matrix fill can be configured to provide controlled release, extended release, sustained release, delayed release, or combinations thereof.

Accordingly, one aspect described herein is a controlled release enteric soft capsule having a shell and a matrix fill, wherein the matrix fill includes an active pharmaceutical ingredient suspended in lipid or lipophilic materials. In another aspect, the lipid or lipophilic material can be a vegetable oil, hydrogenated vegetable oil, fatty acid, wax, fatty acid ester, or a combination thereof.

Accordingly, one embodiment described herein is a controlled release enteric soft capsule having a shell and a matrix fill, wherein the matrix fill includes an active pharmaceutical ingredient.

In one embodiment, the active pharmaceutical ingredient can be dispersed or suspended in the liquid carrier. In one embodiment, the active ingredient can be prepared in a self-emulsifying/microemulsifying drug delivery system (SEDDS/SMEDDS). Optionally, the SEDDS system can include an oil, a surfactant, a cosurfactant or solubilizer, and the active ingredient.

The liquid active ingredients can be prepared to contain the active pharmaceutical ingredient in the range of about 0.005% to about 100%, including all iterations of integers with the specified range, with the balance made up from non-toxic carrier. Methods for preparation of these compositions are known to those skilled in the art. See, for example, *Remington's Pharmaceutical Sciences*, Mack Publishing Company, Easton, Pa., 15th Edition, 1975. The liquid portion of the matrix fill can contain about 0.001% to about 100%, about 0.1% to about 95%, about 1% to about 90%, about 5% to about 70%, or about 10% to about 50% by weight of active ingredient.

In one embodiment descried herein, the enteric soft capsule comprises a matrix fill comprising an active pharmaceutical ingredient comprising at least one or more fatty acids. In one aspect, the matrix fill comprises a pharmaceutical composition comprising one or more PUFAs.

In one embodiment, the oral pharmaceutical composition described herein comprise a matrix fill comprises the composition of Table 8, including all possible iterations of the specified ranges that provide 100% for the total weight percentage.

TABLE 8

Exemplary Fatty Acid (FA) Oil Matrix Fills

| Component | Percent Weight (%) |
| --- | --- |
| Omega-3 FAs | 35-99 |
| Omega-6 FAs | ≤35 |
| EPA | 10-99 |
| DHA | 0-75 |
| DPA | 1-15 |
| EPA and DHA | 40-99 |
| EPA, DHA, and DPA | 40-99 |
| Arachidonic acid | ≤15 |
| Other unsaturated FAs | ≤15 |
| Saturated FAs | ≤3 |
| Antioxidants | 0.01-5 |
| Fat-soluble Vitamins | 0.001-5 |

In one embodiment, the pharmaceutical composition comprises a composition of omega-3 fatty acids comprising at least about 35% to at least about 95% by weight of all fatty acids in the pharmaceutical composition including all iterations of integers within the specified range. In one aspect, pharmaceutical composition comprises a composition of omega-3 fatty acids comprising at least about 35% by weight of all fatty acids in pharmaceutical composition. In another aspect, the pharmaceutical composition comprises a composition of omega-3 fatty acids comprising at least about 40% by weight of all fatty acids in the pharmaceutical composition. In another aspect, the pharmaceutical composition comprises a composition of omega-3 fatty acids comprising at least about 45% by weight of all fatty acids in the pharmaceutical composition. In another aspect, the pharmaceutical composition comprises a composition of omega-3 fatty acids comprising at least about 50% by weight of all fatty acids in the pharmaceutical composition. In another aspect, the omega-3 fatty acids may be a fatty acid, ester, re-esterified triglyceride, or salt thereof.

In another embodiment, the pharmaceutical composition comprises a composition of omega-3 fatty acids comprising of at least about 50% to at least about 85% by weight of all fatty acids in the pharmaceutical composition. In one aspect, the pharmaceutical composition comprises a composition of omega-3 fatty acids comprising at least about 50% by weight of all fatty acids in the pharmaceutical composition. In another aspect, the pharmaceutical composition comprises a composition of omega-3 fatty acids comprising at least about 60% by weight of all fatty acids in the pharmaceutical composition. In another aspect, the pharmaceutical composition comprises a composition of omega-3 fatty acids comprising at least about 70% by weight of all fatty acids in the pharmaceutical composition. In another aspect, the pharmaceutical composition comprises a composition of omega-3 fatty acids comprising at least about 80% by weight of all fatty acids in the pharmaceutical composition. In another aspect, the omega-3 fatty acids may be a fatty acid, ester, re-esterified triglyceride, or salt thereof.

In another embodiment, the pharmaceutical composition comprises a composition of omega-3 fatty acids comprising of at least about 85% to at least about 99% by weight of all fatty acids in the pharmaceutical composition. In one aspect, the pharmaceutical composition comprises a composition of omega-3 fatty acids comprising at least about 85% by weight of all fatty acids in the pharmaceutical composition. In another aspect, the pharmaceutical composition comprises a composition of omega-3 fatty acids comprising at least about 90% by weight of all fatty acids in the pharmaceutical composition. In another aspect, the pharmaceutical composition comprises a composition of omega-3 fatty acids comprising at least about 95% by weight of all fatty acids in the pharmaceutical composition. In another aspect, the pharmaceutical composition comprises a composition of omega-3 fatty acids comprising at least about 99% by weight of all fatty acids in the pharmaceutical composition. In another aspect, the omega-3 fatty acids may be a fatty acid, ester, re-esterified triglyceride, or salt thereof.

In one embodiment, the pharmaceutical composition comprises omega-6 fatty acids in an amount not more than about 20% to not more than about 1% by weight of all fatty acids in the pharmaceutical composition. In one embodiment, the pharmaceutical composition comprises omega-6 fatty acids in an amount not more than about 15% by weight of all fatty acids in the pharmaceutical composition. In one aspect, the pharmaceutical composition comprises omega-6 fatty acids in an amount not more than about 10% by weight of all fatty acids in the pharmaceutical composition. In one aspect, the pharmaceutical composition comprises omega-6 fatty acids in an amount not more than about 7% by weight of all fatty acids in the pharmaceutical composition. In one aspect, the pharmaceutical composition comprises omega-6 fatty acids in an amount not more than about 3% by weight of all fatty acids in the pharmaceutical composition. In one aspect, the pharmaceutical composition comprises omega-6 fatty acids in an amount not more than about 1% by weight of all fatty acids in the pharmaceutical composition. In one aspect, the pharmaceutical composition comprises essentially no omega-6 fatty acids.

In one embodiment, the pharmaceutical composition comprises EPA. In another embodiment, the pharmaceutical composition comprises EPA in an amount of about 10% to about 70% by weight of all fatty acids in the pharmaceutical composition including all iterations of integers within the specified range. In another aspect, the pharmaceutical composition comprises EPA in an amount of about 20% by weight of all fatty acids in the pharmaceutical composition. In another aspect, the pharmaceutical composition comprises EPA in an amount of about 25% by weight of all fatty acids in the pharmaceutical composition. In another aspect, the pharmaceutical composition comprises EPA in an amount of about 30% by weight of all fatty acids in the pharmaceutical composition. In another aspect, the pharmaceutical composition comprises EPA in an amount of about 35% by weight of all fatty acids in the pharmaceutical composition. In another aspect, the pharmaceutical composition comprises EPA in an amount of about 40% by weight of all fatty acids in the pharmaceutical composition. In another aspect, the pharmaceutical composition comprises EPA in an amount of about 45% by weight of all fatty acids in the pharmaceutical composition. In another aspect, the pharmaceutical composition comprises EPA in an amount of about 50% by weight of all fatty acids in the pharmaceutical composition. In another aspect, the pharmaceutical composition comprises EPA in an amount of about 55% by weight of all fatty acids in the pharmaceutical composition. In another aspect, the pharmaceutical composition comprises EPA in an amount of about 60% by weight of all fatty acids in the pharmaceutical composition. In another aspect, the pharmaceutical composition comprises EPA in an amount of about 65% by weight of all fatty acids in the pharmaceutical composition. In another aspect, the pharmaceutical composition comprises EPA in an amount of about 70% by weight of all fatty acids in the pharmaceutical composition. In another aspect, the EPA may be a free fatty acid, ester, re-esterified triglyceride, or salt thereof.

In another embodiment, the pharmaceutical composition comprises EPA in an amount of about 70% to about 99% by weight of all fatty acids in the pharmaceutical composition including all iterations of integers within the specified range. In one aspect, the pharmaceutical composition comprises EPA in an amount of about 75% by weight of all fatty acids in the pharmaceutical composition. In another aspect, the pharmaceutical composition comprises EPA in an amount of about 80% by weight of all fatty acids in the pharmaceutical composition. In another aspect, the pharmaceutical composition comprises EPA in an amount of about 85% by weight of all fatty acids in the pharmaceutical composition. In another aspect, the pharmaceutical composition comprises EPA in an amount of about 90% by weight of all fatty acids in the pharmaceutical composition. In another aspect, the pharmaceutical composition comprises EPA in an amount of about 95% by weight of all fatty acids in the pharmaceutical composition. In another aspect, the pharmaceutical composition comprises EPA in an amount of about 99% by weight of all fatty acids in the pharmaceutical composition. In another aspect, the EPA may be a free fatty acid, ester, re-esterified triglyceride, or salt thereof.

In one embodiment, the pharmaceutical composition comprises EPA with substantially no DHA (e.g., less than about 5% DHA). In one aspect, the EPA may be a free fatty acid, ester, re-esterified triglyceride, or salt thereof.

In one embodiment, the pharmaceutical composition comprises DHA. In another embodiment, the pharmaceutical composition comprises DHA in an amount of about 10% to about 75% by weight of all fatty acids in the pharmaceutical composition including all iterations of integers within the specified range. In another embodiment, the pharmaceutical composition comprises DHA in an amount of about 10% to about 50% by weight of all fatty acids in the pharmaceutical composition including all iterations of integers within the specified range. In one aspect, the pharmaceutical composition comprises DHA in an amount of about 10% by weight of all fatty acids in the pharmaceutical composition. In another aspect, the pharmaceutical composition comprises DHA in an amount of about 15% by weight of all fatty acids in the pharmaceutical composition. In another aspect, the pharmaceutical composition comprises DHA in an amount of about 20% by weight of all fatty acids in the pharmaceutical composition. In another aspect, the pharmaceutical composition comprises DHA in an amount of about 25% by weight of all fatty acids in the pharmaceutical composition. In another aspect, the pharmaceutical composition comprises DHA in an amount of about 30% by weight of all fatty acids in the pharmaceutical composition. In another aspect, the pharmaceutical composition comprises DHA in an amount of about 35% by weight of all fatty acids in the pharmaceutical composition. In another aspect, the pharmaceutical composition comprises DHA in an amount of about 40% by weight of all fatty acids in the pharmaceutical composition. In another aspect, the pharmaceutical composition comprises DHA in an amount of about 45% by weight of all fatty acids in the pharmaceutical composition. In another aspect, the pharmaceutical composition comprises DHA in an amount of about 55% by weight of all fatty acids in the pharmaceutical composition. In another aspect, the pharmaceutical composition comprises DHA in an amount of about 60% by weight of all fatty acids in the pharmaceutical composition. In another aspect, the pharmaceutical composition comprises DHA in an amount of about 65% by weight of all fatty acids in the pharmaceutical composition. In another aspect, the pharmaceutical composition comprises DHA in an amount of about 70% by weight of all fatty acids in the pharmaceutical composition. In another aspect, the pharmaceutical composition comprises DHA in an amount of about 76% by weight of all fatty acids in the pharmaceutical composition. In another aspect, the DHA may be a free fatty acid, ester, re-esterified triglyceride, or salt thereof.

In one embodiment, the pharmaceutical composition comprises DPA. In another embodiment, the pharmaceutical composition comprises DPA in an amount of about 1% to about 15% by weight of all fatty acids in the pharmaceutical composition including all iterations of integers within the specified range. In one aspect, the pharmaceutical composition comprises DPA in an amount of about 1% by weight of all fatty acids in the pharmaceutical composition. In another aspect, the pharmaceutical composition comprises DPA in an amount of about 3% by weight of all fatty acids in the pharmaceutical composition. In another aspect, the pharmaceutical composition comprises DPA in an amount of about 5% by weight of all fatty acids in the pharmaceutical composition. In another aspect, the pharmaceutical composition comprises DPA in an amount of about 7% by weight of all fatty acids in the pharmaceutical composition. In another aspect, the pharmaceutical composition comprises DPA in an amount of about 10% by weight of all fatty acids in the pharmaceutical composition. In another aspect, the pharmaceutical composition comprises DPA in an amount of about 13% by weight of all fatty acids in the pharmaceutical composition. In another aspect, the DPA may be a free fatty acid, ester, re-esterified triglyceride, or salt thereof.

In one embodiment, the pharmaceutical composition comprises EPA and DHA. In another embodiment, the pharmaceutical composition comprises EPA and DHA in an amount of about 45% to about 99% by weight of all fatty acids in the pharmaceutical composition including all iterations of integers within the specified range. In another embodiment, the pharmaceutical composition comprises EPA and DHA in an amount of about 60% to about 99% by weight of all fatty acids in the pharmaceutical composition including all iterations of integers within the specified range. In one aspect, the pharmaceutical composition comprises EPA and DHA in an amount of about 60% by weight of all fatty acids in the pharmaceutical composition. In one aspect, the pharmaceutical composition comprises EPA and DHA in an amount of about 75% by weight of all fatty acids in the pharmaceutical composition. In another aspect, the pharmaceutical composition comprises EPA and DHA in an amount of about 85% by weight of all fatty acids in the pharmaceutical composition. In another aspect, the pharmaceutical composition comprises EPA and DHA in an amount of about 90% by weight of all fatty acids in the pharmaceutical composition. In another aspect, the pharmaceutical composition comprises EPA and DHA in an amount of about 95% by weight of all fatty acids in the pharmaceutical composition. In another aspect, the pharmaceutical composition comprises EPA and DHA in an amount of about 99% by weight of all fatty acids in the pharmaceutical composition. In another aspect, the EPA and DHA may be a free fatty acid, ester, re-esterified triglyceride, or salt thereof.

In one embodiment, the pharmaceutical composition comprises EPA, DHA, and DPA. In another embodiment, the pharmaceutical composition comprises EPA, DHA, and DPA in an amount of about 60% to about 99% by weight of all fatty acids in the pharmaceutical composition including all iterations of integers within the specified range. In another embodiment, the pharmaceutical composition comprises EPA, DHA, and DPA in an amount of about 85% to about 99% by weight of all fatty acids in the pharmaceutical composition including all iterations of integers within the specified range. In one aspect, the pharmaceutical composition comprises EPA, DHA, and DPA in an amount of about 85% by weight of all fatty acids in the pharmaceutical composition. In another aspect, the pharmaceutical composition comprises EPA, DHA, and DPA in an amount of about 90% by weight of all fatty acids in the pharmaceutical composition. In another aspect, the pharmaceutical composition comprises EPA, DHA, and DPA in an amount of about 95% by weight of all fatty acids in the pharmaceutical composition. In another aspect, the pharmaceutical composition comprises EPA, DHA, and DPA in an amount of about 99% by weight of all fatty acids in the pharmaceutical composition. In another aspect, the EPA, DHA, and DPA may be a free fatty acid, ester, re-esterified triglyceride, or salt thereof.

In one embodiment, the pharmaceutical composition comprises a mixture of EPA and DHA with one or more fat soluble vitamins. In one aspect, EPA comprises about 10% to about 70% by weight of the pharmaceutical composition, including each integer within the specified range. In another aspect, DHA comprises about 10% to about 70% by weight of the pharmaceutical composition, including each integer within the specified range. In another aspect, at least another fat soluble vitamin comprises about 0.005% to about 5% by weight of the pharmaceutical composition, including each integer within the specified range. In another aspect, the pharmaceutical composition comprises about 50% EPA and about 20% DHA, and at least another fat soluble vitamin. In another aspect, the pharmaceutical composition comprises at least about 60% EPA and at least about 25% DHA, and at least another fat soluble vitamin. In another aspect, the composition comprises at least about 45% EPA and at least about 20% DHA, and at least another fat soluble vitamin. In another aspect, the composition comprises at least about 46% EPA, at least about 18% DHA, and at least another fat soluble vitamin. In another aspect, the composition comprises at least about 30% EPA, at least about 20% DHA, and at least another fat soluble vitamin. In another aspect, a mixture of EPA and DHA comprising at least about 45% EPA and at least about 18% DHA can be combined in a 99.9:0.1 ratio with cholecalciferol (Vitamin D3) to form a pharmaceutical or nutritional composition; other fat soluble vitamins described herein and known in the art can be added at similar weight percentages. In another aspect, the EPA and DHA may be a free fatty acid, ester, re-esterified triglyceride, or salt thereof.

In another embodiment, the pharmaceutical composition comprises less than about 30%, less than about 20%, less than about 10%, less than about 9%, less than about 8%, less than about 7%, less than about 6%, less than about 5%, less than about 4%, less than about 3%, less than about 2%, less than about 1%, less than about 0.5% or less than about 0.25%, by weight of the total composition or by weight of the total fatty acid content, of any unsaturated fatty acid other than EPA, DHA, or DPA. Illustrative examples of any unsaturated fatty acid other than EPA, DHA, or DPA comprise hexadecatrienoic acid (HTA; all-cis 7,10,13-hexadecatrienoic acid), alpha-linolenic acid (ALA; all-cis-9,12,15-octadecatrienoic acid), stearidonic acid (SDA; all-cis-6,9,12,15,-octadecatetraenoic acid), eicosatrienoic acid (ETE; all-cis-11,14,17-eicosatrienoic acid), eicosatetraenoic acid (ETA; all-cis-8,11,14,17-eicosatetraenoic acid), heneicosapentaenoic acid (HPA; all-cis-6,9,12,15,18-heneicosapentaenoic acid), tetracosapentaenoic acid (all-cis-9,12,15,18,21-tetracosapentaenoic acid), tetracosahexaenoic acid (nisinic acid; all-cis-6,9,12,15,18,21-tetracosahexaenoic acid), linoleic acid (LA; all-cis-9,12-octadecadienoic acid), gamma-linolenic acid (GLA; all-cis-6,9,12-octadecatrienoic acid), Calendic acid (8E,10E,12Z-octadecatrienoic acid), Eicosadienoic acid (all-cis-11,14-eicosadienoic acid), dihomo-gamma linolenic acid (DGLA; all-cis-8,11,14-eicosatrienoic acid), arachidonic acid (AA; all-cis-5,8,11,14-eicosatetraenoic acid), docosadienoic acid (all-cis-13,16-docosadienoic acid), Adrenic acid (all-cis-7,10,13,16-docosatetraenoic acid), docosapentaenoic acid (osbond acid; all-cis-4,7,10,13,16-docosapentaenoic acid), tetracosatetraenoic acid (all-cis-9,12,15,18-tetracosatetraenoic acid), tetracosapentaenoic acid (all-cis-6,9,12,15,18-tetracosapentaenoic acid) and free acids, etheyl esters, or other esters or salts thereof.

In one embodiment, the soft enteric capsules comprising fish oil in the matrix fills described herein are stable for months or years. In one aspect, the pharmaceutical compositions described herein are stable at 25° C. and 60% relative humidity (RH) for about 1 month, about 2 months, about 3 months, about 4 months, about 5 months, about 6 months, about 9 months, about 10 months, about 11 months, about 12 months, or even longer. In another aspect, the pharmaceutical compositions described herein are stable for 1 year or longer at 25° C. and 60% RH. In another aspect, the pharmaceutical compositions described herein are stable for 2 years or longer at 25° C. and 60% RH.

In one embodiment, the pharmaceutical composition described herein is provided as a dosage kit in a dispensing receptacle. In one aspect, the dispensing receptacle is a moisture proof blister pack, strip pack, aluminum blister, transparent or opaque polymer blister with pouch, polypropylene tubes, colored blister materials, tubes, bottles, and bottles optionally containing a child-resistant feature, optionally comprising a desiccant, such as a molecular sieve or a silica gel. In another aspect, the dosage forms are packaged in a dispensing receptacle, which may optionally be packaged together in a box or other enclosure. In another aspect, the dispensing receptacle comprises sufficient amounts of the pharmaceutical composition described herein, for 1 day, 2 days, 6 days, 12 days, 24 days, 30 days, 60 days, or 90 days of dosing. In another aspect, the unit dosage form is about 250 mg to about 5000 mg of the pharmaceutical composition comprising an enteric soft capsule and matrix fill as described herein. In another aspect, the dosage kit comprises 1, 2, 6, 12, 24, 30, 60, 90, 120, 150, 180, 240, 270, or 300 such enteric soft capsules.

In one embodiment, the pharmaceutical composition described herein provides a dosage of a fatty acid composition for administration to a subject. In one embodiment, the fatty acid composition can be administered to a subject without unpleasant side effects, including but not limited to, gastric disturbances such as eructation (belching), bloating, and unpleasant fishy after tastes (e.g., "fishy burps"). The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject can be from ~0 years of age to 99 years of age or older including all iterations of integers within the specified range. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In another embodiment, a pharmaceutical composition is administered to a subject in an amount sufficient to provide a therapeutically effective dose of the fatty acids (e.g., fish oil comprising DHA, EPA, or DPA or a combination thereof) described herein of at least about 1 mg to at least about 10,000 mg, 25 mg at least about 5000 mg, at least about 50 mg to at least about 3000 mg, at least about 75 mg to at least about 2500 mg, or at least about 100 mg to at least about 1000 mg. In one aspect, the pharmaceutical composition is administered to a subject and comprises a therapeutically effective dosage amount of the fatty acids (e.g., fish oil comprising DHA, EPA, or DPA) of at least about 50 mg, at least about 75 mg, at least about 100 mg, at least about 125 mg, at least about 150 mg, at least about 175 mg, at least about 200 mg, at least about 225 mg, at least about 250 mg, at least about 275 mg, at least about 300 mg, at least about 325 mg, at least about 350 mg, at least about 375 mg, at least about 400 mg, at least about 425 mg, at least about 450 mg, at least about 475 mg, at least about 500 mg, at least about 525 mg, at least about 550 mg, at least about 575 mg, at least about 600 mg, at least about 625 mg, at least about 650 mg, at least about 675 mg, at least about 700 mg, at least about 725 mg, at least about 750 mg, at least about 775 mg, at least about 800 mg, at least about 825 mg, at least about 850 mg, at least about 875 mg, at least about 900 mg, at least about 925 mg, at least about 950 mg, at least about 975 mg, at least about 1000 mg, at least about 1025 mg, at least about 1050 mg, at least about 1075 mg, at least about 1100 mg, at least about 1025 mg, at least about 1050 mg, at least about 1075 mg, at least about 1200 mg, at least about 1225 mg, at least about 1250 mg, at least about 1275 mg, at least about 1300 mg, at least about 1325 mg, at least about 1350 mg, at least about 1375 mg, at least about 1400 mg, at least about 1425 mg, at least about 1450 mg, at least about 1475 mg, at least about, 1500 mg, at least about 1525 mg, at least about 1550 mg, at least about 1575 mg, at least about 1600 mg, at least about 1625 mg, at least about 1650 mg, at least about 1675 mg, at least about 1700 mg, at least about 1725 mg, at least about 1750 mg, at least about 1775 mg, at least about 1800 mg, at least about 1825 mg, at least about 1850 mg, at least about 1875 mg, at least about 1900 mg, at least about 1925 mg, at least about 1950 mg, at least about 1975 mg, at least about 2000 mg, at least about 2025 mg, at least about 2050 mg, at least about 2075 mg, at least about 2100 mg, at least about 2125 mg, at least about 2150 mg, at least about 2175 mg, at least about 2200 mg, at least about 2225 mg, at least about 2250 mg, at least about 2275 mg, at least about 2300 mg, at least about 2325 mg, at least about 2350 mg, at least about 2375 mg, at least about 2400 mg, at least about 2425 mg, at least about 2450 mg, at least about 2475 mg, or at least about 2500 mg, at least about 2550 mg, at least about 2575 mg, at least about 2600 mg, at least about 2625 mg, at least about 2650 mg, at least about 2675 mg, at least about 2700 mg, at least about 2725 mg, at least about 2750 mg, at least about 2775 mg, at least about 2800 mg, at least about 2825 mg, at least about 2850 mg, at least about 2875 mg, at least about 2900 mg, at least about 2925 mg, at least about 3000 mg, at least about 3025 mg, at least about 3050 mg, at least about 3075 mg, at least about 3100 mg, at least about 3125 mg, at least about 3150 mg, at least about 3175 mg, at least about 3200 mg, at least about 3225 mg, at least about 3250 mg, at least about 3275 mg, at least about 3300 mg, at least about 3325 mg, at least about 3350 mg, at least about 3375 mg, at least about 3400 mg, at least about 3425 mg, at least about 3450 mg, at least about 3475 mg, at least about 3500 mg, at least about 3525 mg, at least about 3550 mg, at least about 3600 mg, at least about 3625 mg, at least about 3650 mg, at least about 3675 mg, at least about 3700 mg, at least about 3725 mg, at least about 3750 mg, at least about 3775 mg, at least about 3800 mg, at least about 3825 mg, at least about 3850 mg, at least about 3875 mg, at least about 4000 mg, at least about 4025 mg, at least about 4050 mg, at least about 4075 mg, at least about 4100 mg, 4125 mg, at least about 4150 mg, at least about 4175 mg, at least about 4200 mg, at least about 4225 mg, at least about 4250 mg, at least about 4275 mg, at least about 4300 mg, at least about 4325 mg, at least about 4350 mg, at least about 4375 mg, at least about 4400 mg, at least about 4425 mg, at least about 4450 mg, at least about 4475 mg, at least about 4500 mg, at least about 4525 mg, at least about 4550 mg, at least about 4600 mg, at least about 4625 mg, at least about 4650 mg, at least about 4675 mg, at least about 4700 mg, at least about 4725 mg, at least about 4750 mg, at least about 4775 mg, at least about 4800 mg, at least about 4825 mg, at least about 4850 mg, at least about 4875 mg, or at least about 5000 mg.

In one embodiment, the effective amount of fatty acids administered to a patient or subject in need thereof of is at least about 250 mg per dosage. In another embodiment, the effective amount of fatty acids administered to a patient or subject in need thereof is at least about 400 mg per dosage. In another embodiment, the effective amount of fatty acids administered to a patient or subject in need thereof is at least about 500 mg per dosage. In another embodiment, the effective amount of fatty acids administered to a patient or subject in need thereof is at least about 600 mg per dosage. In another embodiment, the effective amount of fatty acids administered to a patient or subject in need thereof is at least about 800 mg per dosage. In another embodiment, the effective amount of fatty acids administered to a patient or subject in need thereof is at least about 900 mg per dosage. In another embodiment, the effective amount of fatty acids administered to a patient or subject in need thereof is at least about 1000 mg per dosage. In another embodiment, the effective amount of fatty acids administered to a patient or subject in need thereof is at least about 1200 mg per dosage. In another embodiment, the effective amount of fatty acids administered to a patient or subject in need thereof is at least about 1400 mg per dosage. In another embodiment, the effective amount of fatty acids administered to a patient or subject in need thereof is at least about 2000 mg per dosage. In another embodiment, the effective amount of fatty acids administered to a patient or subject in need thereof is at least about 3000 mg per dosage. In another embodiment, the effective amount of fatty acids administered to a patient or subject in need thereof is at least about 4000 mg per dosage.

In one embodiment, the pharmaceutical composition is administered in an amount of at least about 250 mg per day. In one embodiment, the pharmaceutical composition is administered in an amount of at least about 500 mg per day. In one embodiment, the pharmaceutical composition is administered in an amount of at least about 1000 mg per day. In another embodiment, the pharmaceutical composition is administered in an amount of at least about 2000 mg per day. In another embodiment, the pharmaceutical composition is administered in an amount of at least about 3000 mg per day. In another embodiment, the pharmaceutical composition is administered in an amount of at least about 4000 mg per day. In another embodiment, the pharmaceutical composition is administered in an amount of at least about 5000 mg per day.

One embodiment described herein is a method for treating, retarding the progression of, delaying the onset of, prophylaxis of, amelioration of, or reducing the symptoms of a disease related to hyperdyslipidemia using a pharmaceutical composition as described herein. Another embodiment described herein is a method for treating, retarding the progression of, delaying the onset of, prophylaxis of, amelioration of, or reducing the symptoms of a cardiovascular-related disease using a pharmaceutical composition as described herein. See U.S. Patent Application Publication No. US 2010/0278879, which is incorporated by reference herein for its specific teachings of treating cardiovascular-related diseases. The term "cardiovascular-related disease" as used herein refers to any disease or disorder of the heart or blood vessels (i.e., arteries and veins) or any symptom thereof. The term "cardiovascular-related disease" as used herein also refers to any disease or disorder of the heart or blood vessels (i.e. arteries and veins) or any symptom thereof, or any disease or condition that causes or contributes to a cardiovascular disease." Non-limiting examples of cardiovascular-related diseases include acute cardiac ischemic events, acute myocardial infarction, angina, angina pectoris, arrhythmia, atrial fibrillation, atherosclerosis, arterial fibrillation, cardiac insufficiency, cardiovascular disease, chronic heart failure, chronic stable angina, congestive heart failure, coronary artery disease, coronary heart disease, deep vein thrombosis, diabetes, diabetes mellitus, diabetic neuropathy, diastolic dysfunction in subjects with diabetes mellitus, edema, essential hypertension, eventual pulmonary embolism, fatty liver disease, heart disease, heart failure, homozygous familial hypercholesterolemia (HoFH), homozygous familial sitosterolemia, hypercholesterolemia, hyperlipidemia, hyperlipidemia in HIV positive subjects, hypertension, hypertriglyceridemia, ischemic complications in unstable angina and myocardial infarction, low blood pressure, metabolic syndrome, mixed dyslipidemia, moderate to mild heart failure, myocardial infarction, obesity management, paroxysmal atrial/arterial fibrillation/fibrillation/flutter, paroxysmal supraventricular tachycardias (PSVT), particularly severe or rapid onset edema, platelet aggregation, primary hypercholesterolemia, primary hyperlipidemia, pulmonary arterial hypertension, pulmonary hypertension, recurrent hemodynamically unstable ventricular tachycardia (VT), recurrent ventricular arrhythmias, recurrent ventricular fibrillation (VF), ruptured aneurysm, sitosterolemia, stroke, supraventricular tachycardia, symptomatic atrial fibrillation/flutter, tachycardia, type II diabetes, vascular disease, venous thromboembolism, ventricular arrhythmias, and other cardiovascular events. The term "treatment" as used herein in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing an enteric soft capsule comprising a pharmaceutical composition using rotary die technology. The thickness of the films or ribbons that form the enteric capsule shell is from about 0.010 inches ($\approx$0.254 mm) to about 0.050 inches ($\approx$1.27 mm), including all integers within the specified range. The shell thickness comprises about 0.010 inch ($\approx$0.254 mm), about 0.015 inch ($\approx$0.381 mm), about 0.02 in ($\approx$0.508 mm), about 0.03 in ($\approx$0.762 mm), about 0.04 in ($\approx$1.02 mm), or about 0.05 in ($\approx$1.27 mm). In one embodiment, the thickness is about 0.02 inches ($\approx$0.508 mm) to about 0.040 inches ($\approx$1.02 mm). In one embodiment, the shell thickness is about 0.028 inches ($\approx$0.711 mm). In another embodiment, the shell thickness is about 0.033 inches ($\approx$0.838 mm). In another embodiment, the shell thickness is about 0.038 inches ($\approx$0.965 mm).

In one embodiment described herein, the enteric soft capsule shell described herein, encapsulates a pharmaceutical composition as described herein. In another embodiment described herein, the enteric soft capsule shell and encapsulated pharmaceutical composition comprises an outer dimension from about 2 oval to about 30 oval including all iterations of capsule sizes within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the enteric soft capsule shell and encapsulated pharmaceutical composition comprises a outer dimension from about 2 round to about 28 round including all iterations of capsule sizes within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated pharmaceutical composition comprises a outer dimension from about 2 oblong to about 22 oblong including all iterations of capsule sizes within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, $1^{st}$ Edition, 2013, which is incorporated by reference herein for such teachings.

In another embodiment described herein, the oral pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The ratios of the mass of any component of any of the formulations disclosed herein to the mass of any other component in the formulation or to the total mass of the other components in the formulation are hereby disclosed as if they were expressly disclosed. All patents and publications cited herein are incorporated by reference herein for the specific teachings thereof.

EXAMPLES

Example 1

All-natural enteric soft capsules as described herein were prepared using the composition shown in Table 9.

TABLE 9

Exemplary Enteric Soft Capsule Formulation

Weight Percentage (%)

| Ingredient | Formula 1 | Formula 2 | Formula 3 | Formula 4 | Formula 5 |
|---|---|---|---|---|---|
| Type A Gelatin | 0 | 33.2 | 0 | 0 | 33.2 |
| Type B Gelatin | 35.4 | 0 | 0 | 0 | 0 |
| Fish Gelatin | 0 | 0 | 35.4 | 0 | 0 |
| Poultry Gelatin | 0 | 0 | 0 | 35.4 | 0 |
| Glycerol | 16 | 16 | 16 | 16 | 16 |
| Pectin | 2.6 | 3.3 | 2.87 | 2.87 | 3.3 |
| Calcium chloride | 0.0057 | 0 | 0 | 0 | 0 |
| Water | 45.8 | 47.5 | 45.8 | 45.8 | 47.5 |
| Supplemental Water | 3 | 3 | 3 | 3 | 3 |
| TOTAL | 103 | 103 | 103 | 103 | 103 |

Example 2

Figure 2:
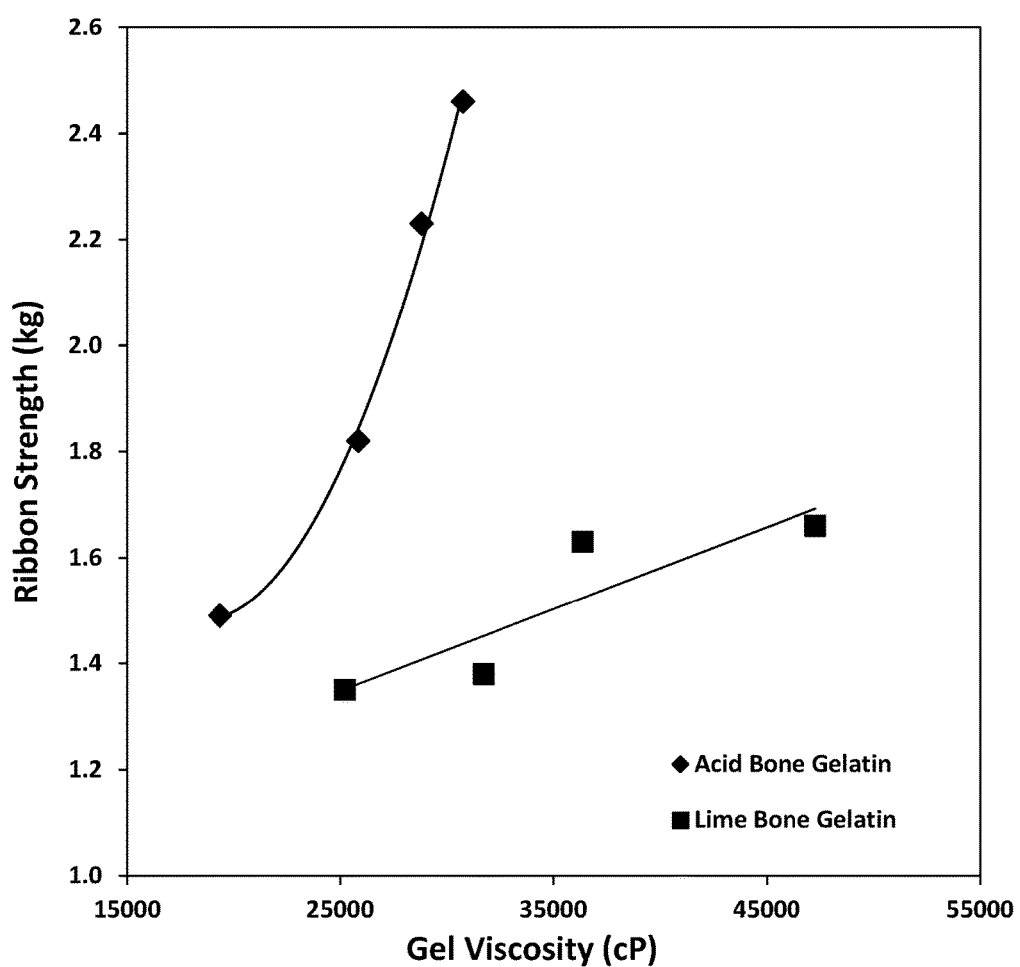
FIG. 2. Ribbon strength versus gel viscosity of the enteric soft capsules comprising the compositions of Table 10.

All-natural enteric soft capsules as described herein were prepared using the composition shown in Table 1. The ribbon strength of the gelatin enteric soft capsule composition comprising different Type A and Type B gelatins shown in Table 10 was assessed after forming ribbons of the gel mass to a thickness of about 0.030 to about 0.045 inches by the methods described herein. The ribbons corresponding to the Type A or Type B gelatin enteric soft capsule composition was allowed to equilibrate at room temperature for 60 minutes. The strength of the ribbons was measured on a texture analyzer and the ribbon strength was normalized to a ribbon thickness of 0.030 inches. The viscosity of the Type A or Type B gelatin enteric soft capsule composition gel mass described herein was measured on a rotary spindle viscometer. The normalized Type A or Type B gelatin enteric soft capsule composition ribbon strength was plotted versus the Type A or Type B gelatin enteric soft capsule composition gel mass viscosity (FIG. 2). The dissolution of the gelatin enteric soft capsule compositions described herein were further tested for dissolution in phosphate buffer at pH 6.8.

TABLE 10

Exemplary Enteric Soft Capsule Formulation

Weight Percentage (%)

| Ingredient | EX 1 | EX 2 | EX 3 | EX 4 | EX 5 | EX 6 | EX 7 | EX 8 |
|---|---|---|---|---|---|---|---|---|
| Type A Gelatin | 0 | 0 | 0 | 0 | 35.4 | 35.4 | 35.4 | 35.4 |
| Type B Gelatin | 35.4 | 35.4 | 35.4 | 35.4 | 0 | 0 | 0 | 0 |
| Glycerol | 16 | 16 | 16 | 16 | 16 | 16 | 16 | 16 |
| Pectin | 2.87 | 2.87 | 3.28 | 3.28 | 2.87 | 2.87 | 3.28 | 3.28 |
| Water | 43 | 46 | 43 | 46 | 43 | 46 | 43 | 46 |
| Supp. Water | 3 | 3 | 3 | 3 | 3 | 3 | 3 | 3 |
| TOTAL | 103 | 103 | 103 | 103 | 103 | 103 | 103 | 103 |

Example 3

Manufacturing Process for All-Natural Enteric Soft Capsule Shells

The all-natural shell components were dispensed into a heated vessel under agitation to generate a heated gel mass. Prior to vacuum deaeration, the heated gel mass was maintained at about 80° C. for a time period of about 0.5 to about 1 hour. Supplemental water was added to compensate for that evaporated/sublimed during the heating/vacuum deaeration. Typically, water comprising about 1-5% by weight of the gel mass was lost during deaeration. In order to compensate for this lost solvent, typically about 3% supplemental water was added to the gel mass prior to deaeration. While mixing, heat and vacuum were applied for 1 to 5 hours. When cooking completes, the gel mass was transferred into another heated vessel and kept at about 60° C. for between 0.5-72 hours. The molten gel mass can be directly transferred to extruders by gravity.

Ribbons were formed via film extrusion. The formed ribbons were fed to a rotary die encapsulation machine to form soft capsules. The wedge temperature was from about 90° C. to about 110° C. The casting drum temperature was about 45° C. The seam formation takes place via adhesion. The formed capsules were dried in a tumbling dryer for between 15-90 minutes, and then dried on trays in a temperature/humidity controlled tunnel for between 12-96 hours.

The process for manufacturing an enteric soft capsule comprising an active pharmaceutical ingredient as described herein includes preparing a gel mass for the enteric soft capsule described herein; casting the gel mass into films or ribbons using heat-controlled drums or surfaces; and manufacturing an enteric soft capsule described herein comprising a matrix fill using rotary die technology. During this process, the matrix fill is injected in to the lumen as the enteric soft capsule described herein is formed by rotary die encapsulation.

The finished enteric soft capsules described herein can withstand USP paddle disintegration tests in acidic media (pH 1.2) for at least 2 hours and release active pharmaceutical ingredients in buffered media (pH 6.8).

Example 4

Examples of gel mass compositions useful for producing all-natural gelatin enteric soft capsules are shown below in Table 11. Composition components are set forth by weight percentage of the total weight of the gel mass composition.

TABLE 11

Exemplary All Natural Enteric Soft Capsule Gel Mass

Weight Percentage (%)

| Ingredient | EX 1 | EX 2 | EX 3 | EX 4 | EX 5 | EX 6 |
|---|---|---|---|---|---|---|
| Type A Gelatin | 26 | 30 | 27 | 34 | 37 | 22 |
| Type B Gelatin | 9 | 5 | 0 | 3 | 0 | 10 |

TABLE 11-continued

Exemplary All Natural Enteric Soft Capsule Gel Mass

| | | | | | | |
|---|---|---|---|---|---|---|
| Gelatin Hydrolysate | 0 | 0 | 1 | 0 | 0 | 0 |
| Plasticizer | 12 | 8 | 14 | 16 | 15.5 | 13 |
| Anionic Polymer | 3 | 3 | 7 | 3.5 | 2 | 3.1 |
| Water | 50 | 54 | 51 | 43.5 | 45.5 | 51.9 |
| Supplemental Water | 1 | 3 | 2 | 5 | 9 | 7 |
| TOTAL | 101 | 103 | 102 | 105 | 109 | 107 |

Components and Relational Ratios

| | | | | | | |
|---|---|---|---|---|---|---|
| Total Gelatin Composition | 35 | 35 | 28 | 37 | 37 | 32 |
| Total Enteric and Gelatin | 38 | 38 | 35 | 40.5 | 39 | 35.1 |
| Total Plasticizer | 12 | 8 | 14 | 16 | 15.5 | 13 |
| Total Gelatin + Anionic Polymer | 38 | 38 | 35 | 40.5 | 39 | 35.1 |
| Ratio Type A to Type B Gelatin | 2.9 | 6 | — | 11.3 | — | 2.2 |
| Ratio Type A Gel. to Gel. Hyd. | — | — | 27 | — | — | — |
| Ratio of Total Gel. to Anion Pol. | 11.7 | 11.7 | 4.0 | 10.6 | 18.5 | 10.3 |
| Ratio of Total Gel. to Plasticizer | 2.9 | 4.4 | 2.0 | 2.3 | 2.4 | 2.5 |
| Ratio of Plast. to Anionic Pol. | 4 | 2.7 | 2.0 | 4.6 | 7.8 | 4.2 |

| | Weight Percentage (%) | | | | | |
|---|---|---|---|---|---|---|
| Ingredient | EX 7 | EX 8 | EX 9 | EX 10 | EX 11 | EX 12 |
| Type A Gelatin | 29 | 31 | 35 | 25 | 28 | 34 |
| Type B Gelatin | 0 | 0 | 0 | 0 | 0 | 0 |
| Gelatin Hydrolysate | 3 | 2.5 | 1 | 0 | 0 | 0 |
| Plasticizer | 19 | 16.4 | 18.7 | 13.7 | 19.5 | 16 |
| Anionic Polymer | 5 | 3.2 | 3.1 | 3.2 | 2.9 | 3.4 |
| Water | 44 | 46.9 | 42.2 | 58.1 | 49.6 | 46.6 |
| Supplemental Water | 4 | 10 | 8 | 1 | 3 | 4 |
| TOTAL | 104 | 110 | 108 | 101 | 103 | 104 |

Components and Relational Ratios

| | | | | | | |
|---|---|---|---|---|---|---|
| Total Gelatin Composition | 32 | 33.5 | 36 | 25 | 28 | 34 |
| Total Enteric and Gelatin | 37 | 36.7 | 39.1 | 28.2 | 30.9 | 37.4 |
| Total Plasticizer | 19 | 16.4 | 18.7 | 13.7 | 19.5 | 16 |
| Total Gelatin + Anionic Polymer | 37 | 36.7 | 39.1 | 28.2 | 30.9 | 37.4 |
| Ratio Type A to Type B Gelatin | — | — | — | — | — | — |
| Ratio Type A Gel. to Gel. Hyd. | 9.7 | 12.4 | 35.0 | — | — | — |
| Ratio of Total Gel. to Anion Pol. | 6.4 | 10.5 | 11.6 | 7.8 | 9.7 | 10 |
| Ratio of Total Gel. to Plasticizer | 1.7 | 2.0 | 1.9 | 1.8 | 1.4 | 2.1 |
| Ratio of Plast. to Anionic Pol. | 3.8 | 5.1 | 6.0 | 4.3 | 6.7 | 4.7 |

Example 5

Examples of all-natural gel mass compositions highlighting the potential use of different plasticizers that are useful for producing gelatin enteric soft capsules are shown below in Table 10. Composition components are set forth by weight percentage of the total weight of the gel mass composition.

TABLE 12

Exemplary All Natural Enteric Soft Capsule Gel Mass

| | Weight Percentage (%) | | | | | |
|---|---|---|---|---|---|---|
| Ingredient | EX 1 | EX 2 | EX 3 | EX 4 | EX 5 | EX 6 |
| Type A Gelatin | 26 | 30 | 27 | 34 | 37 | 22 |
| Type B Gelatin | 9 | 5 | 0 | 3 | 0 | 10 |
| Gelatin Hydrolysate | 0 | 0 | 1 | 0 | 0 | 0 |
| Glycerol | 14 | 16 | 0 | 0 | 0 | 0 |
| Sorbitol | 0 | 0 | 14 | 16 | 0 | 0 |
| Triethyl Citrate | 0 | 0 | 0 | 0 | 14 | 16 |
| Anionic Polymer | 3 | 3 | 3.3 | 3.5 | 2.45 | 3.1 |
| Water | 48 | 46 | 54.7 | 43.5 | 46.55 | 48.9 |
| Supplemental Water | 1 | 3 | 2 | 5 | 9 | 7 |
| TOTAL | 101 | 103 | 102 | 105 | 109 | 107 |

Example 6

Additional enteric soft capsules as described herein were prepared using the composition shown in Table 13.

TABLE 13

Exemplary Enteric Soft Capsule Shell Composition

| Component | Weight Percentage (%) |
|---|---|
| Gelatin | 29.2 |
| Methacrylic Acid Copolymer (EUDRAGIT® L 100) | 11.15 |
| Glycerol | 18 |
| Triethyl citrate | 1.26 |
| NH$_4$OH (30%) | 1.73 |
| Water | 38.62 |

Example 7

Examples of matrix fill formulations useful for gelatin enteric soft capsules are shown below in Table 14. Composition components are set forth by weight percentage of the total weight of the gel mass composition.

TABLE 14

Exemplary Gelatin Soft Capsule Matrix Fill Formulation

| | Weight Percentage (%) | | | | | |
|---|---|---|---|---|---|---|
| Ingredient | EX 1 | EX 2 | EX 3 | EX 4 | EX 5 | EX 6 |
| Lecithin | 0.5 | 3 | 1.5 | 1.5 | 1 | 4 |
| Vegetable oil | 22.1 | 7 | 12.6 | 11 | 35 | 20 |
| Bees wax | 4 | 4 | 2.9 | 2 | 6 | 2.9 |
| Soybean oil | 44.4 | 50 | 14.1 | 35.6 | 35 | 30.1 |
| Chitosan | 7 | 9 | 5 | 5 | 2 | 4 |
| Carbopol® 971 | 2 | 7 | 4 | 5 | 1 | 9 |
| API | 20 | 20 | 60 | 40 | 20 | 30 |
| Matrix Fill Total | 100 | 100 | 100 | 100 | 100 | 100 |

Example 8

Additional examples of matrix fill formulations useful for gelatin enteric soft capsules are shown below in Table 15. Composition components are set forth by weight percentage of the total weight of the gel mass composition.

TABLE 15

Exemplary Gelatin Soft Capsule Matrix Fill Formulation

| | Weight Percentage (%) | | | | | | |
|---|---|---|---|---|---|---|---|
| Ingredient | EX 1 | EX 2 | EX 3 | EX 4 | EX 5 | EX 6 | EX 7 |
| Polyethylene glycol | 84 | 10 | 85 | 35 | 33 | 47 | 22 |
| Glycerol | 3 | 0 | 6 | 10 | 5 | 0 | 5 |
| Propylene glycol | 0 | 5 | 0 | 3 | 0 | 10 | 0 |
| Water | 3 | 5 | 4 | 7 | 5 | 20 | 5 |
| API | 11 | 80 | 5 | 45 | 57 | 23 | 68 |
| Matrix Fill Total | 100 | 100 | 100 | 100 | 100 | 100 | 100 |

Example 9

Examples of matrix fill formulation specifications useful for enteric soft capsules described herein are shown below in Table 16. Composition components are set forth by weight.

TABLE 16

Exemplary Gelatin Soft Capsule Matrix Fill Formulation

| | Weight (mg) | | | | | | |
|---|---|---|---|---|---|---|---|
| Ingredient | EX 1 | EX 2 | EX 3 | EX 4 | EX 5 | EX 6 | EX 7 |
| Diclofenac | 25 | 75 | 75 | 25 | 125 | 150 | 175 |
| Total Fill Weight | 83 | 270 | 220 | 422 | 220 | 350 | 220 |
| Ratio Diclofenac to Fill | 0.30 | 0.27 | 0.34 | 0.06 | 0.57 | 0.43 | 0.80 |

Example 10

Enteric soft capsules with a matrix fill comprising diclofenac as described herein were prepared using the composition shown in Table 17 and were tested in a two stage delayed release experiment. For the assessment of gastric resistance in the first stage of the experiment, the gelatin enteric soft capsule composition and matrix fill described herein was placed in 900 mL of 0.1 N HCl pre-equilibrated to 37° C. Samples were taken at 15 min, 30 min, 45 min, and 60 min time points. The samples were syringe filtered and HPLC was run to detect diclofenac release. For the assessment of diclofenac delayed release at a pH of about 6.8 in the second stage of the experiment, the gelatin enteric soft capsule composition and matrix fill described herein that had been incubating in 900 mL of 0.1 N HCl pre-equilibrated to 37° C. was removed from the 0.1 N HCl and placed in 900 mL of 0.05 M phosphate buffer at pH 6.8. Samples were taken at 75 min, 90 min, 105 min, 120 min, 150 min, 180 min, 210 min, 360 min, and at 24-hour time points relative to the beginning of the first stage of the experiment. The samples were syringe filtered and HPLC was run to detect diclofenac release. The percentage of diclofenac release from the gelatin enteric soft capsule composition and matrix fill described herein was calculated at each time point for the two tested buffers (FIG. 1).

TABLE 17

Exemplary Gelatin Enteric Soft Capsule Shell with Matrix Fill Formulation

| Ingredient | Weight (kg) | % Weight |
|---|---|---|
| Type A Gelatin | 4.814 | 33.2 |
| Glycerol | 2.3 | 16 |

TABLE 17-continued

Exemplary Gelatin Enteric Soft Capsule Shell with Matrix Fill Formulation

| Ingredient | Weight (kg) | % Weight |
|---|---|---|
| Pectin | 0.48 | 3.3 |
| Water | 6.89 | 47.5 |
| Supplemental Water | 0.44 | 3 |
| Enteric Soft Capsule Shell TOTAL | 14.5 | 103% |
| Lecithin | 0.007 | 1.45 |
| Vegetable oil | 0.056 | 12.56 |
| Bees wax | 0.013 | 2.9 |
| Soybean oil | 0.239 | 53.1 |
| Chitosan | 0.023 | 5 |
| Carbopol ® 971 | 0.023 | 5 |
| Diclofenac potassium | 0.09 | 20 |
| Matrix Fill Total | 0.451 | 100 |

Example 11

Figure 3:
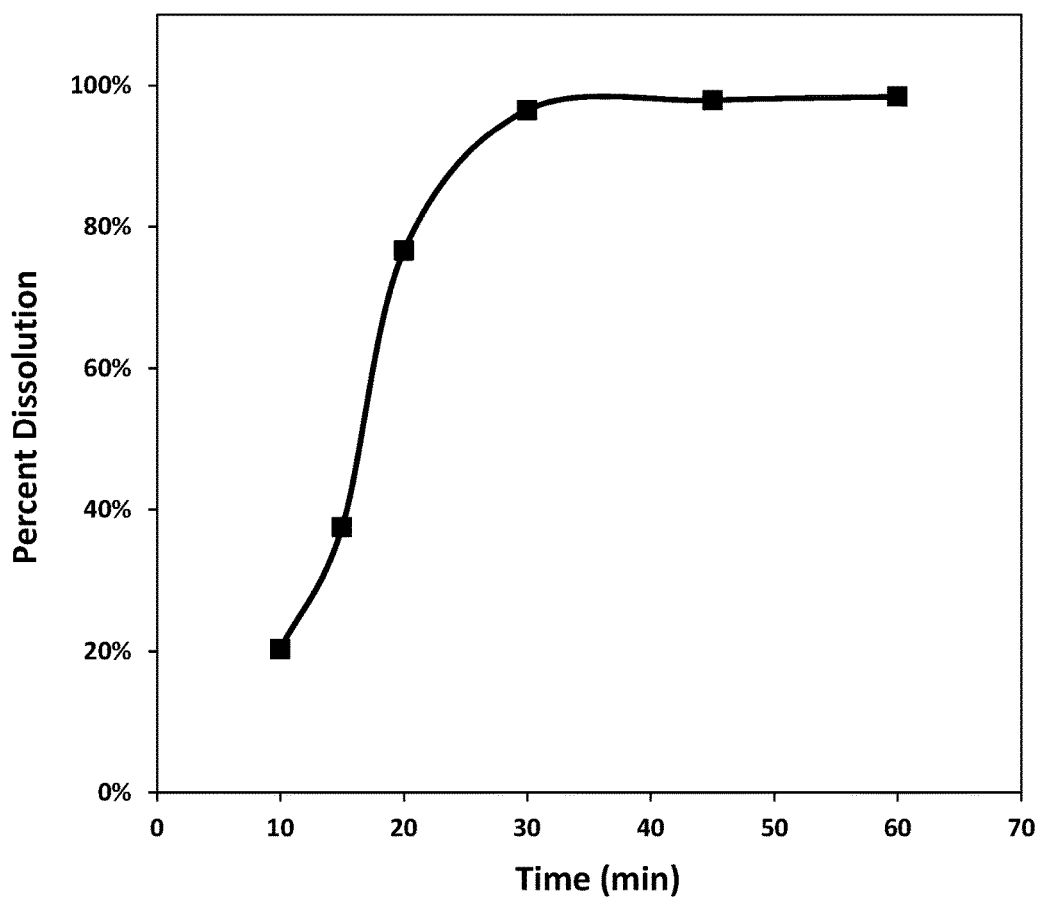
FIG. 3. Dissolution of enteric soft capsules in pH 6.8 phosphate buffer comprising diclofenac (average of six experiments).

Enteric soft capsules with a matrix fill comprising diclofenac as described herein were prepared using the composition shown in Table 18. The dissolution of the gelatin enteric soft capsule compositions shown in Table 18 were further tested for dissolution in phosphate buffer at pH 6.8 (FIG. 3).

TABLE 18

Exemplary Gelatin Enteric Soft Capsule and Matrix Fill Formulations

| Shell Ingredient | Weight Percentage (%) |
|---|---|
| Type A Gelatin | 36.07 |
| Glycerol | 16.26 |
| Pectin | 3.34 |
| Water | 44.30 |
| Supplemental Water | 3 |
| Shell Total | 103 |

| | Weight Percentage (%) | | | | | |
|---|---|---|---|---|---|---|
| Fill Ingredient | EX 1 | EX 2 | EX 3 | EX 4 | EX 5 | EX 6 |
| Polyethylene glycol 600 | 79 | 67 | 56 | 45 | 33 | 33 |
| Diclofenac | 11 | 23 | 34 | 45 | 57 | 57 |
| Glycerol | 5 | 0 | 5 | 0 | 5 | 0 |
| Propylene glycol | 0 | 5 | 0 | 5 | 0 | 5 |
| Water | 5 | 5 | 5 | 5 | 5 | 5 |
| Matrix Fill Total | 100 | 100 | 100 | 100 | 100 | 100 |

Example 12

Enteric soft capsules with a matrix fill comprising diclofenac as described herein were prepared using the composition shown in Table 19 and were tested in simulated gastric fluid (SGF) for at least 1 hour and simulated intestinal fluid (SIF) for at least 1 hour. The enteric capsules were further tested for 2 hours in 0.1 N HCl and for 1 hour in phosphate buffer pH 6.8.

TABLE 19

Exemplary Gelatin Enteric Soft Capsule and Matrix Fill Formulations

| Shell Ingredient | Weight Percentage (%) | |
| --- | --- | --- |
| Type A Gelatin | 36.07 | |
| Glycerol | 16.26 | |
| Pectin | 3.34 | |
| Water | 44.30 | |
| Supplemental Water | 3 | |
| Shell Total | 103 | |
| Fill Ingredient | Weight % | Weight/cap (mg) |
| Polyethylene glycol 600 | 63 | 170.1 |
| Diclofenac | 27 | 72.9 |
| Propylene glycol | 5 | 13.5 |
| Water | 5 | 13.5 |
| Matrix Fill Total | 100 | 270 |

TABLE 19-continued

Exemplary Gelatin Enteric Soft Capsule and Matrix Fill Formulations

| Disintegration testing results (n = 12 capsules) | |
| --- | --- |
| Disintegration (1 hr SGF) | PASS (n = 12/12) |
| Disintegration (1 hr SIF) | PASS (n = 12/12) |
| Disintegration (1 hr phosphate buffer pH 6.8) | PASS (n = 12/12) |

Example 13

Examples of fish oil fill compositions useful in enteric soft capsules described herein are shown below in Table 20. Composition components are set forth by weight percentage of the total weight of the fill composition.

TABLE 20

Exemplary Fish Oil Fill Compositions (1000 mg)

| | Weight Percentage (%) | | | | | |
| --- | --- | --- | --- | --- | --- | --- |
| Ingredient | EX 1 | EX 2 | EX 3 | EX 4 | EX 5 | EX 6 |
| EPA | 90 | 94 | 59 | 53 | 47 | 38 |
| DHA | ≤10 | ≤5 | 19 | 20 | 38 | 45 |
| DPA | ≤5 | ≤5 | 6 | 5.5 | ≤5 | ≤5 |
| Arachidonic acid | ≤5 | ≤5 | 2 | 3 | ≤5 | ≤5 |
| Other unsaturated FAs | ≤5 | ≤5 | ≤15 | ≤15 | ≤15 | ≤15 |
| Antioxidant | 0.5 | 0.1 | 0.25 | 0.5 | 0.25 | 0.25 |
| Total | 100 | 100 | 100 | 100 | 100 | 100 |

Example 14

Examples of fish oil fill compositions useful in enteric soft capsules described herein are shown in Table 21. Composition components are set forth by weight of the total weight of the fill composition.

TABLE 21

Exemplary Fish Oil Fill Compositions

| | Composition (mg) | | | | | |
| --- | --- | --- | --- | --- | --- | --- |
| Ingredient | EX 1 | EX 2 | EX 3 | EX 4 | EX 5 | EX 6 |
| EPA | 180 | 360 | 540 | 720 | 180 | 360 |
| DHA | 70 | 140 | 210 | 280 | 70 | 140 |
| Fat Soluble Vitamin | 0.001 | 0.001 | N/A | N/A | 0.001 | 0.002 |
| Total | 250 | 500 | 750 | 1000 | 250 | 500 |

| | Composition (mg) | | | | | |
| --- | --- | --- | --- | --- | --- | --- |
| Ingredient | EX 7 | EX 8 | EX 9 | EX 10 | EX 11 | EX 12 |
| EPA | 180 | 360 | 162 | 420 | 325 | 650 |
| DHA | 70 | 140 | 108 | 250 | 215 | 250 |
| Total Omega-3 | 250 | 500 | 300 | 700 | 600 | 900 |
| Other Fish Oil | 160 | 320 | 300 | 300 | 600 | 500 |
| Fat Soluble Vitamin | 0.001 | 0.002 | 0.002 | 0.002 | 0.002 | 0.002 |
| Total | 410 | 820 | 600 | 1000 | 1200 | 1400 |

What is claimed:

1. An enteric soft capsule gel mass composition consisting of:
   (a) about 33% to about 36% Type A gelatin by mass;
   (b) about 3.3% pectin by mass;
   (c) about 16% glycerol by mass; and
   the viscosity of the gel mass composition comprises about 20,000 cP to about 30,000 cP.

2. The composition of claim 1, wherein upon extrusion to a ribbon, the ribbon comprises a strength of about 1.5 kg to about 2.5 kg.

3. The composition of claim 1, wherein the Type A gelatin has a Bloom strength of about 150 grams to about 350 grams.

4. The capsule of claim 1, wherein the Type A gelatin comprises acid bone gelatin or pig skin gelatin.

5. The composition of claim 1, wherein the Type A gelatin comprises acid bone gelatin.

6. The composition of claim 1, wherein the Type A gelatin comprises pig skin gelatin.

7. The composition of claim 1, wherein the ribbon comprises a thickness of about 0.03 inches to about 0.045 inches.

8. A method for preparing the enteric soft capsule of claim 1, the method comprising:
   combining the gelatin, pectin, glycerol and water with heating to form a gel mass; and
   (ii) forming an enteric soft capsule from the gel mass using rotary die technology further comprising a fill comprising one or more active ingredients.

9. The enteric soft capsule formed by the method of claim 7.

10. The capsule of claim 8, wherein the capsule shell does not dissolve in simulated gastric fluid (pH 1.2) for at least 2 hours, and begins dissolution in simulated intestinal fluid (pH 6.8) within about 10 minutes.

11. The capsule of claim 8, wherein the capsule comprises a fill comprising one or more active ingredients.

12. The capsule of claim 8, wherein the capsule comprises a fill of fish oil or non-steroidal anti-inflammatory drug.

13. An enteric soft capsule comprising a shell and a matrix, the shell consisting of:
   (a) about 33% to about 36% Type A gelatin by mass;
   (b) about 3.3% pectin by mass;
   (c) about 16% glycerol by mass; and
   the capsule shell comprises a strength of about 1.5 kg to about 2.5 kg.

14. The capsule of claim 13, wherein the Type A gelatin comprises acid bone gelatin or pig skin gelatin.

15. The capsule of claim 13, wherein the matrix comprises one or more active ingredients.

16. The capsule of claim 13, wherein the capsule shell does not dissolve in simulated gastric fluid (pH 1.2) for at least 2 hours, and begins dissolution in simulated intestinal fluid (pH 6.8) within about 10 minutes.

17. The capsule of claim 14, wherein the active ingredient comprises fish oil or on a non-steroidal anti-inflammatory drug.

18. The capsule of claim 17, where in the fish oil comprises eicosapentaenoic acid (EPA), docosahexaenoic acid (DHA), and one or more fat-soluble vitamins.

19. The capsule of claim 17, wherein the non-steroidal anti-inflammatory drug comprises diclofenac.

\* \* \* \* \*